United States Patent
Wasmuth et al.

(10) Patent No.: US 9,650,383 B2
(45) Date of Patent: May 16, 2017

(54) ALDOSE REDUCTASE INHIBITORS AND USES THEREOF

(71) Applicant: THE TRUSTEES OF COLUMBIA UNIVERSITY IN THE CITY OF NEW YORK, New York, NY (US)

(72) Inventors: Andrew Wasmuth, New York, NY (US); Donald W. Landry, New York, NY (US); Shi Xian Deng, White Plains, NY (US); Banavara L. Mylari, East Lyme, CT (US); Ravichandran Ramasamy, Ardsley, NY (US); Ann Marie Schmidt, Franklin Lakes, NJ (US)

(73) Assignee: THE TRUSTEES OF COLUMBIA UNIVERSITY IN THE CITY OF NEW YORK, New York, NY (US)

( * ) Notice: Subject to any disclaimer, the term of this patent is extended or adjusted under 35 U.S.C. 154(b) by 92 days.

(21) Appl. No.: 14/541,365

(22) Filed: Nov. 14, 2014

(65) Prior Publication Data
US 2015/0072989 A1 Mar. 12, 2015

Related U.S. Application Data

(60) Division of application No. 13/742,573, filed on Jan. 16, 2013, now Pat. No. 8,916,563, which is a continuation-in-part of application No. PCT/US2011/044038, filed on Jul. 14, 2011.

(60) Provisional application No. 61/365,098, filed on Jul. 16, 2010.

(51) Int. Cl.
C07D 487/04 (2006.01)

(52) U.S. Cl.
CPC .................. C07D 487/04 (2013.01)

(58) Field of Classification Search
CPC .................................................. C07D 487/04
See application file for complete search history.

(56) References Cited

U.S. PATENT DOCUMENTS

| | | | |
|---|---|---|---|
| 4,939,140 A | 7/1990 | Larson et al. | |
| 4,954,629 A | 9/1990 | Mylari et al. | |
| 4,996,204 A | 2/1991 | Mylari et al. | |
| 5,155,259 A | 10/1992 | Suzuki et al. | |
| 5,304,557 A | 4/1994 | Mylari | |
| 5,677,342 A | 10/1997 | Malamas et al. | |
| 6,159,976 A | 12/2000 | Lambert et al. | |
| 6,570,013 B2 | 5/2003 | Mylari | |
| 6,579,879 B2 | 6/2003 | Mylari | |
| 6,849,629 B2 | 2/2005 | Mylari | |
| 7,572,910 B2 | 8/2009 | Mylari | |
| 2006/0293265 A1 | 12/2006 | Srivastava et al. | |

FOREIGN PATENT DOCUMENTS

| | | |
|---|---|---|
| EP | 0397350 A1 | 11/1990 |
| EP | 0401981 A1 | 12/1990 |
| FR | 2647676 A1 | 12/1990 |
| JP | S62-114988 A | 5/1987 |
| JP | H01-216975 A | 8/1989 |
| JP | H03005481 | 1/1991 |
| JP | 2003-155274 A | 5/2003 |
| JP | 5934206 B2 | 6/2016 |
| WO | WO-91/09019 A1 | 6/1991 |
| WO | WO 2012/009553 | 1/2012 |

OTHER PUBLICATIONS

Hwang et al. "Central role for aldose reductase pathway in myocardial ischemic injury" The FASEB Journal, Aug. 2004, vol. 18, No. 11, pp. 1192-1199.*
Office Action mailed on Nov. 25, 2014 for co-pending CN Application No. 201180034944.5; 12 pages.
Cannon, Joseph G., "Chapter Nineteen: Analog Design," Burger's Medicinal Chemistry and Drug Discovery: Fifth Edition, vol. 1: Principles and Practice, Wiley-Interscience, pp. 783-802, 28 pages (1995).
Extended European Search Report in related Application No. 11807523.3, dated Oct. 2, 2013, 6 pages.
International Search Report and Written Opinion for PCT/US11/44038, dated Dec. 6, 2011, 8 pages.
International Search Report and Written Opinion Issued by the U.S. Patent and Trademark Office as International Searching Authority for International Application No. PCT/US14/11465 mailed Apr. 16, 2014 (9 pgs.).
Kinoshita JH. A thirty year journey in the polyol pathway. Exp Eye Res. Jun. 1990;50(6):567-73.
Mylari, B.L. et al., "Orally Active Aldose Reductase Inhibitors: Indazoleacetic, Oxopyridazineacetic, and Oxopyridazineacetic Acid Derivatives." J. Med. Chem. 1992, 35:2155-2162.
Mylari, Banavara L., et al., "Novel, Potent Aldose Reductase Inhibitors: 3,4-Dihydro-4-oxo-3-[[5-(trifluoromethyl)-2-benzothiazolyl]methyl]-1-phthalazine-acetic Acid (Zopolrestat) and Congeners", J. Med. Chem., 1991, vol. 34, pp. 108-122.
Mylari, Banavara L., et al., "Potent, Orally Active Aldose Reductase Inhibitors Related to Zopolrestat: Surrogates for Benzothiazole Side Chain", J. Med. Chem., 1992, vol. 35, pp. 457-465.

(Continued)

Primary Examiner — Kendra D Carter
(74) Attorney, Agent, or Firm — Wilmer Cutler Pickering Hale and Dorr LLP

(57) ABSTRACT

The present invention relates to novel compounds and pharmaceutical compositions thereof, and methods for promoting healthy aging of skin, the treatment of skin disorders, the treatment of cardiovascular disorders, the treatment of renal disorders, the treatment of angiogenesis disorders, such as cancer, treatment of tissue damage, such as non-cardiac tissue damage, the treatment of evolving myocardial infarction, and the treatment of various other disorders, such as complications arising from diabetes with the compounds and compositions of the invention. Other disorders can include, but are not limited to, atherosclerosis, coronary artery disease, diabetic nephropathy, diabetic neuropathy, diabetic retinopathy, infections of the skin, peripheral vascular disease, stroke, and the like.

24 Claims, 3 Drawing Sheets

(56) References Cited

OTHER PUBLICATIONS

Roy, Thomas M., et al., "The effect of an aldose reductase inhibitor on cardiovascular performance in patients with diabetes mellitus", Diabetes Research and Clinical Practice, 1990, vol. 10, pp. 91-97.

Sheridan, Robert P., "The Most Common Replacements in Drug-Like Compounds," J. Chem. Inf. Comput. Sci., vol. 42, pp. 103-108 (2002).

Wilson DK et al. Refined 1.8 A structure of human aldose reductase complexed with the potent inhibitor zopolrestat. Proc Natl Aced Sci U S A. Nov. 1, 1993;90(21):9847-51.

Japanese Office Action issued by the Japan Patent Office for Application No. 2013-520752 dated May 25, 2015 (7 pages).

English Translation of Notice of Reasons for Rejection issued Nov. 7, 2016 for corresponding Japanese Patent Application No. 2016-005570 (5 pages).

* cited by examiner

ALDOSE REDUCTASE INHIBITORS AND USES THEREOF

This application is a divisional of U.S. patent application Ser. No. 13/742,573, filed Jan. 16, 2013, which was filed as a continuation-in-part of International Application Number PCT/US2011/044038, filed Jul. 14, 2011, which claims priority to U.S. Provisional Patent Application No. 61/365,098, filed Jul. 16, 2010, the contents of each of which are hereby incorporated by reference in their entireties.

All patents, patent applications and publications cited herein are hereby incorporated by reference in their entirety. The disclosures of these publications in their entireties are hereby incorporated by reference into this application in order to more fully describe the state of the art as known to those skilled therein as of the date of the invention described and claimed herein.

This patent disclosure contains material that is subject to copyright protection. The copyright owner has no objection to the facsimile reproduction by anyone of the patent document or the patent disclosure as it appears in the U.S. Patent and Trademark Office patent file or records, but otherwise reserves any and all copyright rights.

FIELD OF THE INVENTION

The present invention relates to novel compounds and pharmaceutical compositions thereof, and methods for promoting healthy aging of skin, the treatment of skin disorders, the treatment of cardiovascular disorders, the treatment of renal disorders, the treatment of angiogenesis disorders, such as cancer, treatment of tissue damage, such as non-cardiac tissue damage, the treatment of evolving myocardial infarction, and the treatment of various other disorders, such as complications arising from diabetes with the compounds and compositions of the invention. Other disorders can include, but are not limited to, atherosclerosis, coronary artery disease, diabetic nephropathy, diabetic neuropathy, diabetic retinopathy, infections of the skin, peripheral vascular disease, stroke, and the like.

BACKGROUND OF THE INVENTION

Diabetes is one of the most common chronic disorders, in which high blood glucose levels result from a lack of insulin production and/or insulin sensitivity. Individuals with high blood glucose metabolize more glucose via a glucose to sorbitol to fructose pathway in insulin insensitive cells such as lenses, peripheral nerves and glomerulus. This leads to an overabundance of sorbitol in the cells, which is not easily diffused through the cell membrane. The increased concentration of sorbitol triggers an influx of water into the cells, causing swelling and potential damage.

Aldose reductase, an enzyme present in many parts of the body, catalyzes the reduction of glucose to sorbitol, one of the steps in the sorbitol pathway that is responsible for fructose formation from glucose. Aldose reductase activity increases as the glucose concentration rises in diabetic conditions where tissues are no longer insulin sensitive. These tissues include, for example, lenses, peripheral nerves and glomerulus of the kidney. Sorbitol cannot easily diffuse through cell membranes and therefore accumulates, causing osmotic damage, which in turn leads to retinopathy, neuropathy, and nephropathy. Therefore, inhibition of aldose reductase could prevent the buildup of sorbitol in insulin insensitive cells in diabetics, and presents a novel method to prevent the macrovascular and microvascular complications in diabetic patients. In addition, aldose reductase inhibitors, such as zopolrestat, may aid in treating or ameliorating such effects and have shown efficacy in wound healing in the corneal epithelium of diabetic animal models.

SUMMARY OF THE INVENTION

In one aspect, the present invention is directed to compounds of formula (I)

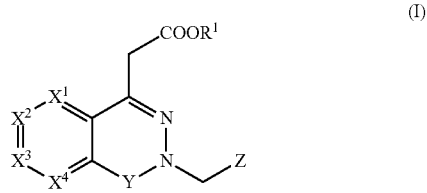

wherein,
$R^1$ is H, $(C_1-C_6)$-alkyl, $(C_1-C_6)$-hydroxyalkyl, or $(C_1-C_6)$-aminoalkyl;
$X^1$ is N or $CR^3$;
$X^2$ is N or $CR^4$;
$X^3$ is N or $CR^5$;
$X^4$ is N or $CR^6$; with the proviso that two or three of $X^1$, $X^2$, $X^3$, or $X^4$ are N;
Y is a bond, C=O, C=S, C=NH, or C=N$(C_1-C_4)$-alkyl;
Z is

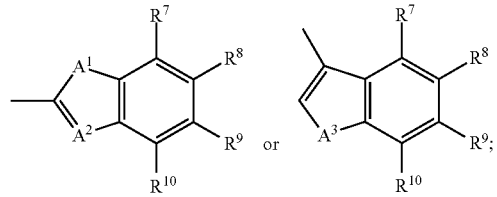

$A^1$ is $NR^{11}$, O, S or $CH_2$;
$A^2$ is N or CH;
$A^3$ is $NR^{11}$, O, or S;
$R^3$ through $R^{10}$ are independently hydrogen, halogen, cyano, acyl, haloalkyl, haloalkoxy, haloalkylthio, trifluoroacetyl, $(C_1-C_4)$-alkyl, $(C_1-C_4)$-alkoxy, $(C_1-C_4)$-alkylthio, $(C_1-C_4)$-alkylsulfinyl, or $(C_1-C_4)$-alkylsulfonyl; or two of $R^3$ through $R^6$ or two of $R^7$ through $R^{10}$ taken together are $(C_1-C_4)$-alkylenedioxy; and
$R^{11}$ is hydrogen, $C_1-C_4$ alkyl, or C(O)O—$(C_1-C_4)$-alkyl; or pharmaceutically acceptable salts or solvates thereof.

In another aspect, the present invention is also directed to pharmaceutical compositions comprising a compound of formula (I), or a pharmaceutically acceptable salt or solvent thereof.

In yet another aspect, the present invention is also directed to methods of treatment comprising administration of a compound of formula (I) or a pharmaceutically acceptable salt or solvent thereof, or pharmaceutical compositions comprising a compound of formula (I), or a pharmaceutically acceptable salt or solvent thereof, to a subject in need thereof. The compounds and/or compositions of the invention may be useful, for example, in promoting healthy aging of skin, the treatment of skin disorders, the treatment of angiogenesis disorders, such as cancer, the treatment of tissue damage, the treatment of cardiovascular disorders, the treatment of renal disorders, the treatment of evolving myocardial infarction, the treatment of various other disorders, such as complications arising from diabetes. Such disorders can include, but are not limited to, atherosclerosis, coronary artery disease, diabetic nephropathy, diabetic neuropathy, diabetic retinopathy, infections of the skin, peripheral vascular disease, stroke, and the like.

In still another aspect, the invention is directed to processes for preparing compounds of formula (I).

The present invention is based, in part, on certain discoveries which are described more fully in the Examples section of the present application. For example, the present invention is based, in part, on the discovery of compounds of formula (I) and the aldose reductase inhibition exhibited by such compounds.

These and other embodiments of the invention are further described in the following sections of the application, including the Detailed Description, Examples, and Claims. Still other objects and advantages of the invention will become apparent by those of skill in the art from the disclosure herein, which are simply illustrative and not restrictive. Thus, other embodiments will be recognized by the ordinarily skilled artisan without departing from the spirit and scope of the invention.

DETAILED DESCRIPTION OF THE INVENTION

Figure 1:
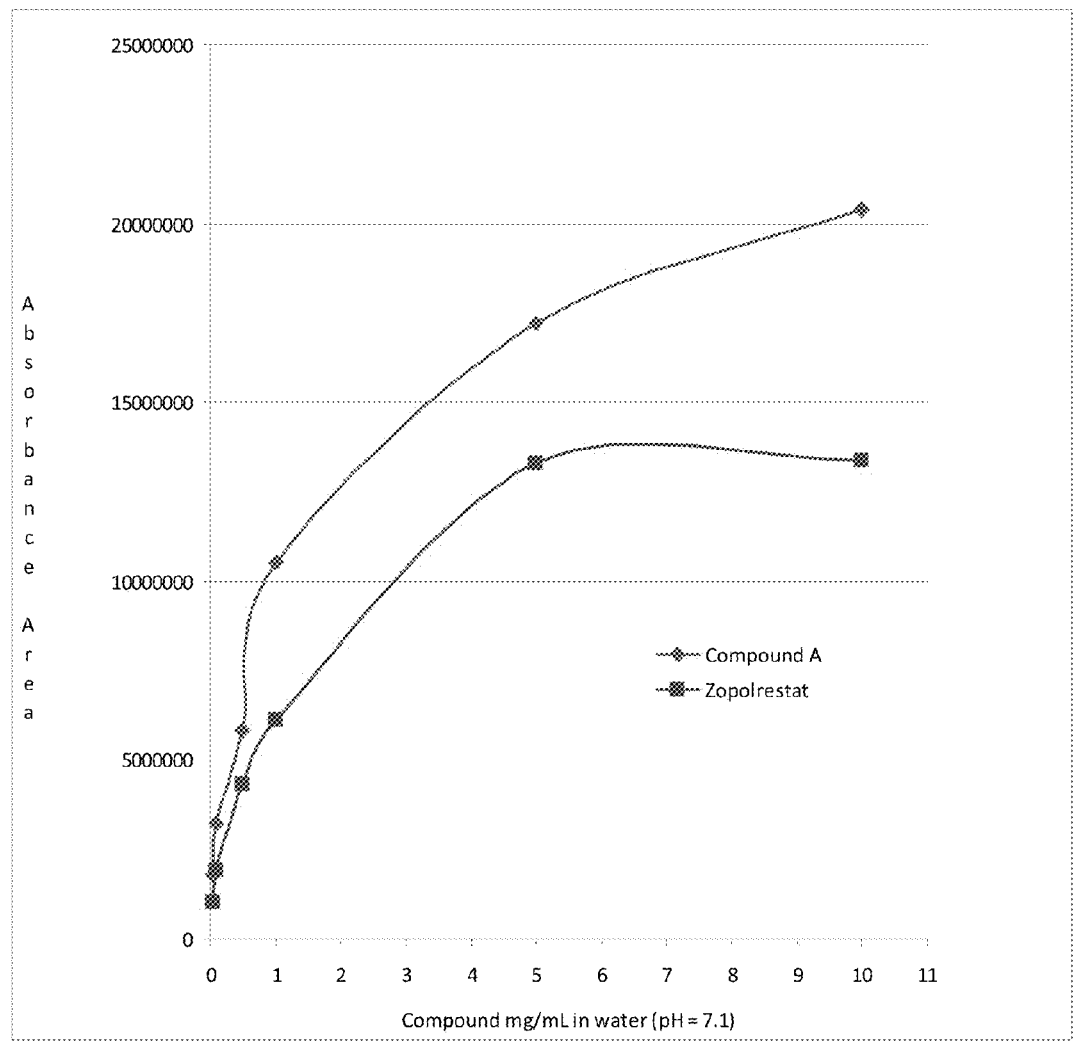
FIG. 1 is a solubility curve for Compound A and zopolrestat in aqueous solution.

Aldose reductase inhibitors are described, for example, in U.S. Pat. Nos. 5,677,342; 5,155,259; 4,939,140; U.S. patent application Ser. No. 11/210,283; and Roy et al., in Diabetes Research and Clinical Practice, Vol. 10, Issue 1, 91-97; and references cited therein; each of which hereby incorporated by reference in its entirety. Aldose reductase inhibitors include, for example, zopolrestat, epalrestat, ranirestat, berberine and sorbinil. A novel family of aldose reductase inhibitors has been discovered and is described herein. Surprisingly, this novel family comprises compounds that exhibit dramatically improved properties such as, for example, binding affinity, solubility and polarity relative to other aldose reductase inhibitors such as, for example, zopolrestat. Compounds such as zopolrestat are described, for example in U.S. Pat. Nos. 4,939,140; 6,159,976; and 6,570,013; each of which hereby incorporated by reference in its entirety. The inventors have also surprisingly discovered that changes in functionalities at positions that often reside in a hydrophobic binding pocket of the enzyme do not abolish binding of the compounds to the enzyme. For example, incorporation of a polar moiety such as, for example, a nitrogen atom in the phenyl ring of the phthalazine, results in improvement of binding affinity and solubility. This is unexpected, in part due to the propensity of the phenyl ring of the phthalazine to occupy a hydrophobic pocket in the enzyme.

The compounds and/or compositions of the invention may be effective in treating, reducing, and/or suppressing complications related to aldose reductase activity such as, for example, neuropathy, retinopathy, nephropathy and multiple complications in diabetic patients. The compounds and/or compositions of the invention may also be effective in treating, reducing, and/or reducing cardiovascular and renal disorders in non-diabetic patients, as well as promoting healthy aging of skin or wound healing.

Abbreviations and Definitions

The term "aldose reductase inhibitor" refers to compounds and salts or solvates thereof that function by inhibiting the activity of the enzyme aldose reductase, which is primarily responsible for regulating metabolic reduction of aldoses. Exemplary aldoses include, but are not limited to, glucose or galactose, and their corresponding polyols, such as sorbitols and galactitols. Exemplary aldose reductase inhibitors may be found in U.S. Pat. Nos. 4,939,140; 4,954,629; and 5,304, 557; each of which hereby incorporated by reference in its entirety.

The term "compound of the invention" as used herein means a compound of formula (I). The term is also intended to encompass salts, hydrates, pro-drugs and solvates thereof.

The term "composition(s) of the invention" as used herein means compositions comprising a compound of the invention, and salts, hydrates, pro-drugs, or solvates thereof. The compositions of the invention may further comprise other agents such as, for example, excipients, stabilants, lubricants, solvents, and the like.

The term "alkyl", as used herein, unless otherwise indicated, refers to a monovalent aliphatic hydrocarbon radical having a straight chain, branched chain, monocyclic moiety, or polycyclic moiety or combinations thereof, wherein the radical is optionally substituted at one or more carbons of the straight chain, branched chain, monocyclic moiety, or polycyclic moiety or combinations thereof with one or more substituents at each carbon, where the one or more substituents are independently $C_1$-$C_{10}$ alkyl. Examples of "alkyl" groups include methyl, ethyl, propyl, isopropyl, butyl, isobutyl, sec-butyl, tert-butyl, pentyl, hexyl, heptyl, cyclopropyl, cyclobutyl, cyclopentyl, cyclohexyl, cycloheptyl, norbornyl, and the like.

The term "halogen", as used herein, means chlorine (Cl), fluorine (F), iodine (I) or bromine (Br).

The term "method(s) of the invention" as used herein means methods comprising treatment with the compounds and/or compositions of the invention.

The term "solvate" as used herein means a compound, or a pharmaceutically acceptable salt thereof, wherein molecules of a suitable solvent are incorporated in the crystal lattice. A suitable solvent is physiologically tolerable at the dosage administered. Examples of suitable solvents are ethanol, water and the like. When water is the solvent, the molecule is referred to as a "hydrate."

A "pharmaceutical composition" refers to a mixture of one or more of the compounds described herein, or pharmaceutically acceptable salts, solvates, pro-drugs or hydrates thereof, with other chemical components, such as physiologically acceptable carriers and excipients. The purpose of a pharmaceutical composition is to facilitate administration of a compound to an organism or subject.

A "pro-drug" or "pro-drug" refers to an agent which is converted into the parent drug in vivo. Pro-drugs are often useful because, in some situations, they are easier to administer than the parent drug. They are bioavailable, for instance, by oral administration whereas the parent drug is either less bioavailable or not bioavailable. The pro-drug also has improved solubility in pharmaceutical compositions over the parent drug. For example, the compound carries protective groups which are split off by hydrolysis in body fluids, e.g., in the bloodstream, thus releasing active compound or is oxidized or reduced in body fluids to release the compound. The term "pro-drug" may apply to such functionalities as, for example, the acid functionalities of the compounds of formula I. Pro-drugs may be comprised of structures wherein a acid group is masked, for example, as an ester or amide. Further examples of pro-drugs are discussed herein and, for example, by Alexander et al., *J. Med. Chem.* 1988, 31, 318 (hereby incorporated by reference in its entirety).

The term "pharmaceutically acceptable salt" is intended to include salts derived from inorganic or organic acids including, for example hydrochloric, hydrobromic, sulfuric, nitric, perchloric, phosphoric, formic, acetic, lactic, maleic, fumaric, succinic, tartaric, glycolic, salicylic, citric, methanesulfonic, benzenesulfonic, benzoic, malonic, trifluoroacetic, trichloroacetic, naphthalene-2 sulfonic and other acids; and salts derived from inorganic or organic bases including, for example sodium, potassium, calcium, ammonium or tetrafluoroborate. Exemplary pharmaceutically acceptable salts are found, for example, in Berge, et al. (*J. Pharm. Sci.* 1977, 66(1), 1; and U.S. Pat. Nos. 6,570,013 and 4,939,140; each hereby incorporated by reference in its entirety). Pharmaceutically acceptable salts are also intended to encompass hemi-salts, wherein the ratio of compound: acid is respectively 2:1. Exemplary hemi-salts are those salts derived from acids comprising two carboxylic acid groups, such as malic acid, fumaric acid, maleic acid, succinic acid, tartaric acid, glutaric acid, oxalic acid, adipic acid and citric acid. Other exemplary hemi-salts are those salts derived from diprotic mineral acids such as sulfuric acid. Exemplary preferred hemi-salts include, but are not limited to, hemimaleate, hemifumarate, and hemisuccinate.

The term "acid" contemplates all pharmaceutically acceptable inorganic or organic acids. Inorganic acids include mineral acids such as hydrohalic acids, such as hydrobromic and hydrochloric acids, sulfuric acids, phosphoric acids and nitric acids. Organic acids include all pharmaceutically acceptable aliphatic, alicyclic and aromatic carboxylic acids, dicarboxylic acids, tricarboxylic acids, and fatty acids. Preferred acids are straight chain or branched, saturated or unsaturated C1-C20 aliphatic carboxylic acids, which are optionally substituted by halogen or by hydroxyl groups, or C6-C12 aromatic carboxylic acids. Examples of such acids are carbonic acid, formic acid, fumaric acid, acetic acid, propionic acid, isopropionic acid, valeric acid, alpha-hydroxy acids, such as glycolic acid and lactic acid, chloroacetic acid, benzoic acid, methane sulfonic acid, and salicylic acid. Examples of dicarboxylic acids include oxalic acid, malic acid, succinic acid, tataric acid and maleic acid. An example of a tricarboxylic acid is citric acid. Fatty acids include all pharmaceutically acceptable saturated or unsaturated aliphatic or aromatic carboxylic acids having 4 to 24 carbon atoms. Examples include butyric acid, isobutyric acid, sec-butyric acid, lauric acid, palmitic acid, stearic acid, oleic acid, linoleic acid, linolenic acid, and phenylsteric acid. Other acids include gluconic acid, glycoheptonic acid and lactobionic acid.

As used herein the term "about" is used herein to mean approximately, roughly, around, or in the region of. When the term "about" is used in conjunction with a numerical range, it modifies that range by extending the boundaries above and below the numerical values set forth. In general, the term "about" is used herein to modify a numerical value above and below the stated value by a variance of 20 percent up or down (higher or lower).

An "effective amount", "sufficient amount" or "therapeutically effective amount" as used herein is an amount of a compound that is sufficient to effect beneficial or desired results, including clinical results. As such, the effective amount may be sufficient, for example, to reduce or ameliorate the severity and/or duration of afflictions related to aldose reductase, or one or more symptoms thereof, prevent the advancement of conditions or symptoms related to afflictions related to aldose reductase, or enhance or otherwise improve the prophylactic or therapeutic effect(s) of another therapy. An effective amount also includes the amount of the compound that avoids or substantially attenuates undesirable side effects.

As used herein and as well understood in the art, "treatment" is an approach for obtaining beneficial or desired results, including clinical results. Beneficial or desired clinical results may include, but are not limited to, alleviation or amelioration of one or more symptoms or conditions, diminution of extent of disease or affliction, a stabilized (i.e., not worsening) state of disease or affliction, preventing spread of disease or affliction, delay or slowing of disease or affliction progression, amelioration or palliation of the disease or affliction state and remission (whether partial or total), whether detectable or undetectable. "Treatment" can also mean prolonging survival as compared to expected survival if not receiving treatment.

The phrase "in need thereof" refers to the need for symptomatic or asymptomatic relief from conditions related to aldose reductase activity or that may otherwise be relieved by the compounds and/or compositions of the invention.

The term "carrier" refers to a diluent, adjuvant, excipient, or vehicle with which a compound is administered. Non-limiting examples of such pharmaceutical carriers include liquids, such as water and oils, including those of petroleum, animal, vegetable or synthetic origin, such as peanut oil, soybean oil, mineral oil, sesame oil and the like. The pharmaceutical carriers may also be saline, gum acacia, gelatin, starch paste, talc, keratin, colloidal silica, urea, and the like. In addition, auxiliary, stabilizing, thickening, lubricating and coloring agents may be used. Other examples of suitable pharmaceutical carriers are described in Remington's Pharmaceutical Sciences (Alfonso Gennaro ed., Krieger Publishing Company (1997); Remington's: The Science and Practice of Pharmacy, 21$^{st}$ Ed. (Lippincot, Williams & Wilkins (2005); Modern Pharmaceutics, vol. 121 (Gilbert Banker and Christopher Rhodes, CRC Press (2002); each of which hereby incorporated by reference in its entirety).

The terms "animal," "subject" and "patient" as used herein include all members of the animal kingdom including, but not limited to, mammals (e.g., mice, rats, cats, monkeys, dogs, horses, swine, etc.) and humans.

In one embodiment, aldose reductase inhibitors described herein encompass compounds of formula (I) or pharmaceutically acceptable salts, pro-drugs and solvates thereof,

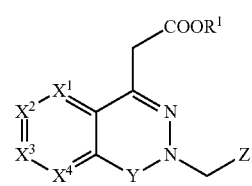

(I)

wherein, $R^1$ is H, $(C_1-C_6)$-alkyl, $(C_1-C_6)$-hydroxyalkyl, or $(C_1-C_6)$-aminoalkyl;

$X^1$ is N or $CR^3$;

$X^2$ is N or $CR^4$;

$X^3$ is N or $CR^5$;

$X^4$ is N or $CR^6$; with the proviso that two or three of $X^1$, $X^2$, $X^3$, or $X^4$ are N;

Y is a bond, C=O, C=S, C=NH, or C=N($C_1$-$C_4$)-alkyl;

Z is

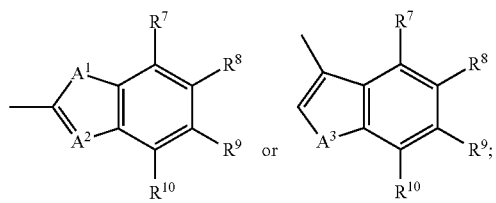

$A^1$ is $NR^{11}$, O, S or $CH_2$;

$A^2$ is N or CH;

$A^3$ is $NR^{11}$, O, or S;

$R^3$ through $R^{10}$ are independently hydrogen, halogen, cyano, acyl, haloalkyl, haloalkoxy, haloalkylthio, trifluoroacetyl, $(C_1-C_4)$-alkyl, $(C_1-C_4)$-alkoxy, $(C_1-C_4)$-alkylthio, $(C_1-C_4)$-alkylsulfinyl, or $(C_1-C_4)$-alkylsulfonyl; or two of $R^3$ through $R^6$ or two of $R^7$ through $R^{10}$ taken together are $(C_1-C_4)$-alkylenedioxy; and $R^{11}$ is hydrogen, $C_1$-$C_4$ alkyl, or C(O)O—$(C_1-C_4)$-alkyl.

It will be recognized by those of skill in the art that the designation of

Z is

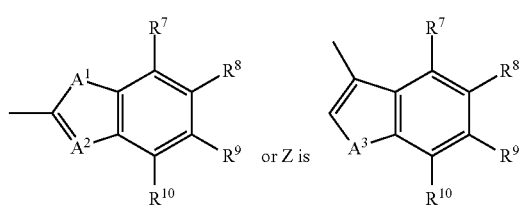

indicates that when Z is

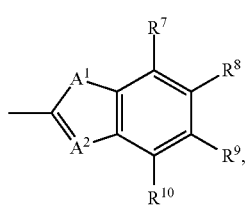

the compounds of formula (I) are understood to encompass

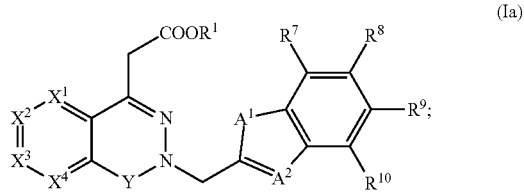

and when Z is

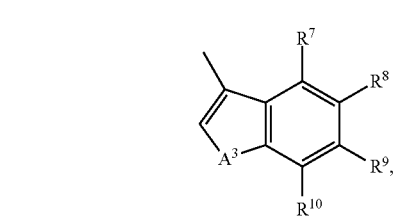

the compounds of formula (I) are understood to encompass

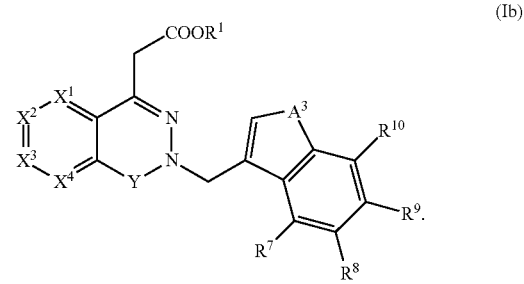

In certain embodiments, $R^1$ is hydrogen or $(C_1-C_6)$-alkyl. In certain embodiments, $R^1$ is hydrogen. In certain embodiments, $R^1$ is $(C_1-C_6)$-alkyl. In certain embodiments, $R^1$ is tert-butyl.

In certain embodiments, $R^3$ through $R^{10}$ are independently hydrogen, halogen or haloalkyl. In certain embodiments, $R^3$ through $R^{10}$ are independently hydrogen, halogen or trihaloalkyl.

In certain embodiments, $R^3$ through $R^6$ are hydrogen.

In certain embodiments, $R^7$ through $R^{10}$ are independently hydrogen, halogen or haloalkyl. In certain embodiments, $R^7$ through $R^{10}$ are independently hydrogen, halogen or trihaloalkyl.

In certain embodiments, $R^7$ and $R^{10}$ are hydrogen.

In certain embodiments, $R^8$ is hydrogen, halogen or haloalkyl. In certain embodiments, $R^8$ is hydrogen. In certain embodiments, $R^8$ is halogen. In certain embodiments, $R^8$ is haloalkyl.

In certain embodiments, $R^9$ is hydrogen, halogen or haloalkyl. In certain embodiments, $R^9$ is hydrogen. In certain embodiments, $R^9$ is halogen. In certain embodiments, $R^9$ is haloalkyl.

In certain embodiments, Y is C=O, C=S, C=NH, or C=N($C_1$-$C_4$)-alkyl. In certain embodiments, Y is C=O or C=S. In certain embodiments, Y is C=O. In certain embodiments, Y is C=S. In certain embodiments, Y is C=NH, or C=N($C_1$-$C_4$)-alkyl.

In certain embodiments, $A^1$ is $NR^{11}$, S or $CH_2$. In certain embodiments, $A^1$ is $NR^{11}$ or O. In certain embodiments, $A^1$ is $NR^{11}$ or S. In certain embodiments, $A^1$ is $NR^{11}$. In certain embodiments, $A^1$ is O. In certain embodiments, $A^1$ is S.

In certain embodiments, $A^2$ is N or CH. In certain embodiments, $A^1$ is N. In certain embodiments, $A^1$ is CH.

In certain embodiments, $A^3$ is O or S. In certain embodiments, $A^3$ is O. In certain embodiments, $A^3$ is S.

In certain embodiments, $X^1$ and $X^4$ are nitrogen.
In certain embodiments, $X^1$ and $X^2$ are nitrogen.
In certain embodiments, $X^1$ and $X^3$ are nitrogen.
In certain embodiments, $X^2$ and $X^3$ are nitrogen.
In certain embodiments, $X^2$ and $X^4$ are nitrogen.
In certain embodiments, $X^3$ and $X^4$ are nitrogen.
In certain embodiments, Z is

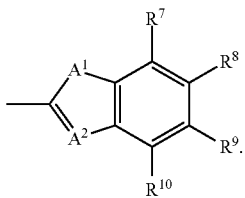

In certain embodiments, Z is

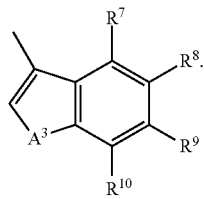

In certain embodiments, $R^1$ is hydrogen or $(C_1-C_6)$-alkyl;
$X^1$ and $X^4$ are N;
$X^2$ is $CR^4$;
$X^3$ is $CR^5$;
Y is C=O;
Z is

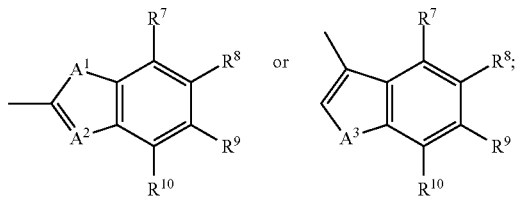

$A^1$ is $NR^{11}$, O, or S;
$A^2$ is N;
$A^3$ is O, or S;
$R^4$ and $R^5$ are hydrogen;
$R^7$ through $R^{10}$ are independently hydrogen, halogen, cyano, acyl, haloalkyl, haloalkoxy, haloalkylthio, $(C_1-C_4)$-alkyl, $(C_1-C_4)$-alkoxy, $(C_1-C_4)$-alkylthio, $(C_1-C_4)$-alkylsulfinyl, or $(C_1-C_4)$-alkylsulfonyl; and
$R^{11}$ is hydrogen, $C_1-C_4$ alkyl, or $C(O)O-(C_1-C_4)$-alkyl.

In certain embodiments, $R^1$ is hydrogen or tert-butyl;
$X^1$ and $X^4$ are N;
$X^2$ is $CR^4$;
$X^3$ is $CR^5$;
Y is C=O;
Z is

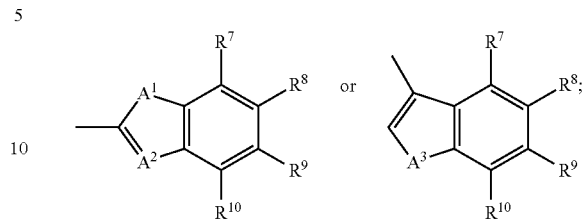

$A^1$ is $NR^{11}$, O or S;
$A^2$ is N;
$A^3$ is O or S;
$R^4$ and $R^5$ are hydrogen;
$R^7$ through $R^{10}$ are independently hydrogen, halogen, or haloalkyl; and
$R^{11}$ is hydrogen, $(C_1-C_4)$-alkyl, or C(O)O-tert-butyl.

In certain embodiments, $R^1$ is hydrogen or tert-butyl;
$X^1$ and $X^4$ are N;
$X^2$ is CH;
$X^3$ is CH;
Y is C=O;
Z is

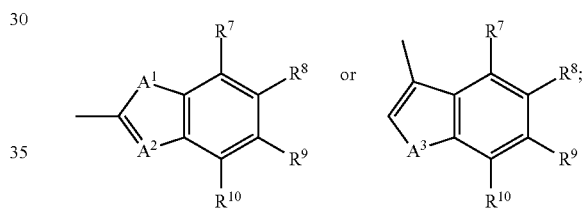

$A^1$ is $NR^{11}$, O or S;
$A^2$ is N;
$A^3$ is O or S;
$R^7$, $R^8$ and $R^{10}$ are independently hydrogen, halogen, or haloalkyl;
$R^9$ is halogen, or haloalkyl; and
$R^{11}$ is hydrogen or methyl.

In certain embodiments, $R^1$ is hydrogen or tert-butyl;
$X^1$ and $X^4$ are N;
$X^2$ is CH;
$X^3$ is CH;
Y is C=O;
Z is

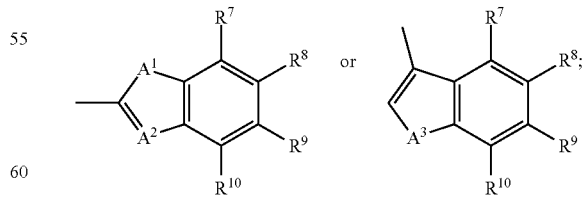

$A^1$ is $NR^{11}$, O or S;
$A^2$ is N;
$A^3$ is O or S;
$R^7$, $R^8$ and $R^{10}$ are independently hydrogen, halogen, or haloalkyl;

$R^9$ is chlorine, or trifluoromethyl; and $R^{11}$ is hydrogen or methyl.

In certain embodiments, the compounds of formula (I) encompass Compound A or pharmaceutically acceptable salts thereof, such as mono-, di-, or tri-ethanolamine salts.

Compound A

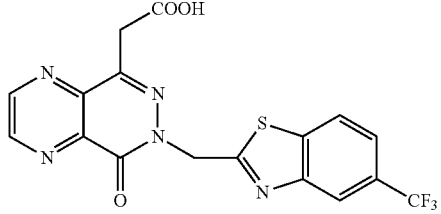

In certain embodiments, the compounds of formula (I) encompass Compound B or pharmaceutically acceptable salts thereof, such as mono-, di-, or tri-ethanolamine salts.

Compound B

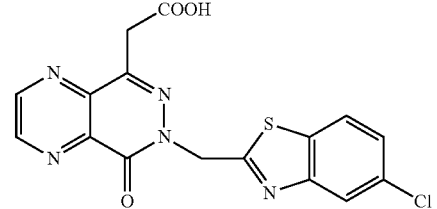

Synthesis

The compounds of formula (I) can generally be prepared, for example, according to Scheme 1.

where $X^1$, $X^2$, $X^3$, $X^4$, $R^1$, $A^1$, $A^2$, $R^3$ through $R^{11}$ are defined as above and Q is a halogen, such as Cl, Br, I, and the like, or any other leaving group, such as OH, $OSO_2Me$, OMs, OTs, OTf, and the like.

In certain embodiments, the reaction can be carried out in the presence of a base, such as potassium tert-butoxide, sodium hydride, sodium methoxide, sodium ethoxide, and the like.

In certain embodiments, the reaction can be carried out using aprotic solvents, such as DMF, THF, NMP, and the like. In certain embodiments, the reaction can be carried out using alcohol solvents, such as methanol, ethanol, and the like.

In certain embodiments, the reaction can be carried out at temperatures of between about 5° C. to about 80° C., such as 20° C. to 30° C.

In certain embodiments, the reaction can be subsequently followed by further separation and purification steps, such as chromatography (e.g., flash, HPLC, MPLC, etc.), crystallization, and the like.

Other suitable reactions are possible, such as hydrolysis of the compound of formula (I) in to obtain different forms of the compound of formula (I). For example, compounds having tert-butoxy, methoxy, ethoxy, and the like group as $R^1$ can be hydrolyzed by reacting with a suitable reagent, such as trifluoroacetic acid (TFA), HCl, KOH, or the like, to obtain a compound of formula (I) having hydrogen as $R^1$.

The compounds of formula (I) can also generally be prepared according to Scheme 2.

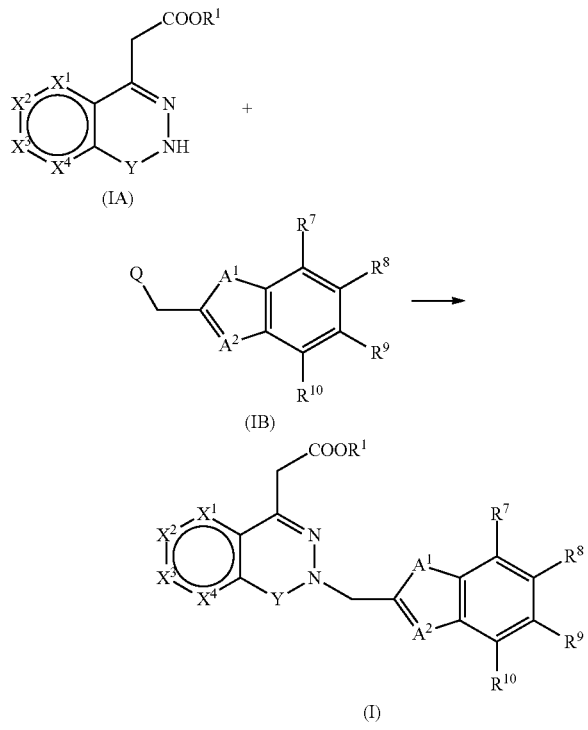

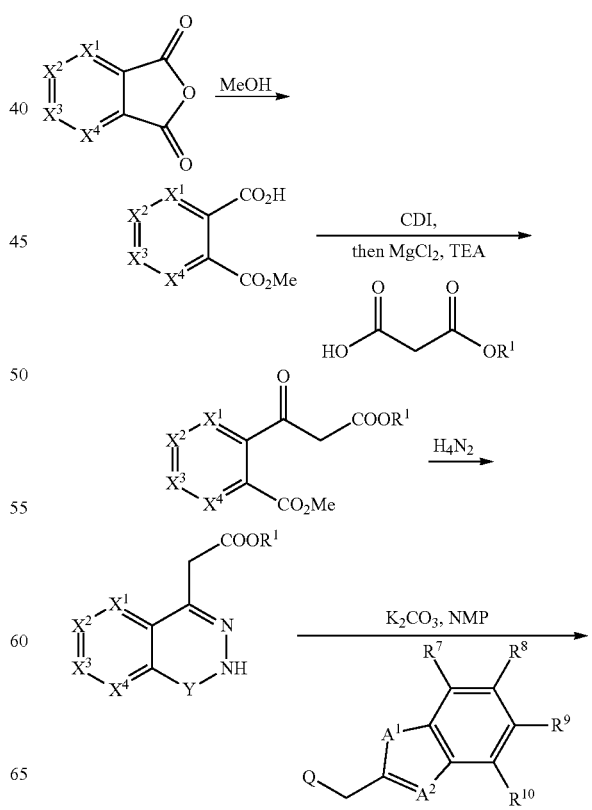

-continued

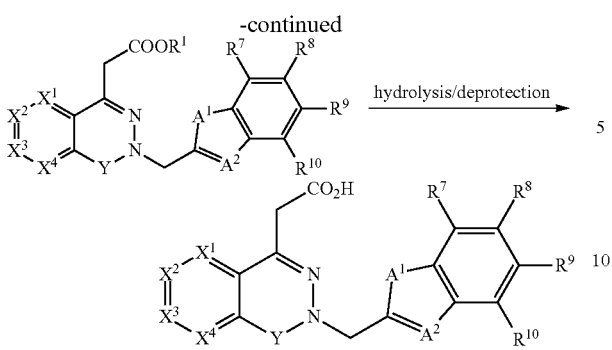

For example, the following exemplary synthesis can be carried out according to Scheme 3.

Scheme 3.

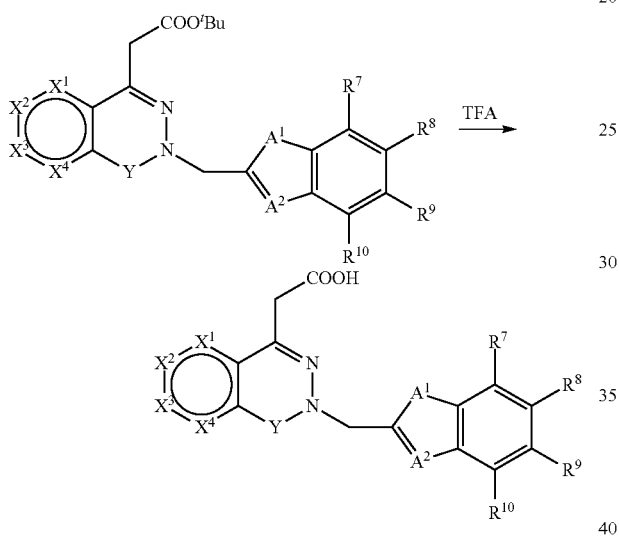

In some other embodiments, where Y is C═O, subsequent reactions can be carried out to replace C═O with C═S or C═N, or the like.

Compound of Formula (IB)

To obtain compounds of Formula (IB), different possibilities exist. For example, commercial sources, such as Sigma-Aldrich may be available. Alternatively, compounds of Formula (IB) can be synthesized by a variety of different reactions, such as a condensation reaction as schematically illustrated below in Scheme 4. The reaction can be carried out using a variety of solvents, such as ethanol, methanol, DMF, AcOH, and the like. The reaction can be carried out at temperatures of between about 5° C. to about 80° C., such as, for example, 55° C. to 65° C.

Scheme 4.

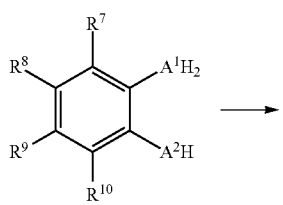

-continued

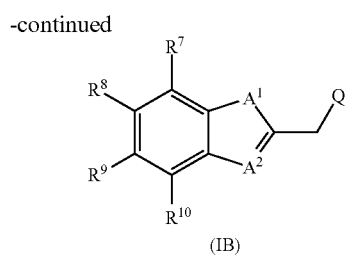

(IB)

Additional exemplary descriptions regarding synthesis of certain compounds of Formula (IB) are described in *J. Med. Chem.* (1991), Vol. 34, pp. 108-122 and *J. Med. Chem.* (1992), Vol. 35, No. 3, pp. 457-465; each of which hereby incorporated by reference in its entirety.

Compounds of Formula (IA)

To obtain compounds of Formula (IA), different possibilities exist. For example, compounds of Formula (IA) can be synthesized as shown in Scheme 5. For example, to obtain a compound of Formula (IA) when Y is C═O, reaction of a compound represented by Formula (IIA) with a reagent that cause addition-cyclization reaction, such reaction with hydrazine or the like, can be carried out as shown below. The reaction can be carried out using a variety of solvents, such as ethanol, methanol, THF, and the like. The reaction can be carried out at temperatures of between about 20° C. to about 100° C., such as 60° C. to 80° C.

Scheme 5.

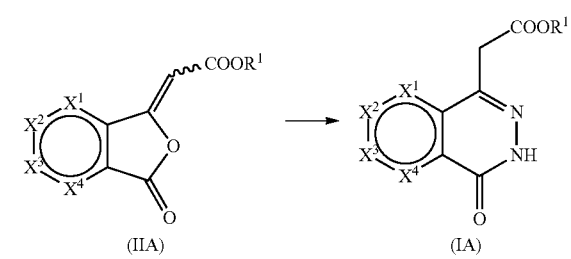

(IIA)          (IA)

The compounds of Formula (IIA) can be obtained, for example, by a reaction of an anhydride with a reagent that causes a Wittig reaction, such as (tert-butoxycarbonylmethylene)-triphenylphosphorane, and the like, as shown in Scheme 6. The reaction can be carried out using aprotic solvents, such as CH$_2$Cl$_2$, THF, 1,4-dioxane, toluene, and the like. The reaction can be carried out at temperatures of between about 20° C. to about 110° C., such as 55° C. to 70° C.

Scheme 6.

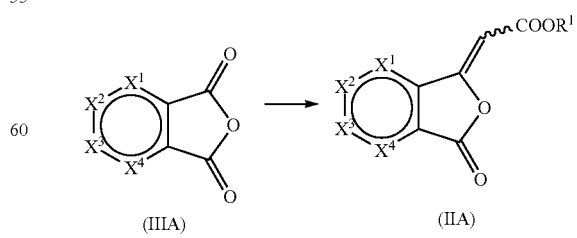

(IIIA)          (IIA)

In certain embodiments, reaction of an anhydride with a reagent that causes a Wittig reaction can lead to a mixture of the particular compounds represented by Formula (IIA), as exemplified below (Scheme 7). In such instances, if necessary, the mixture can be separated and purified to obtain the particular compounds of Formula (IIA) of interest.

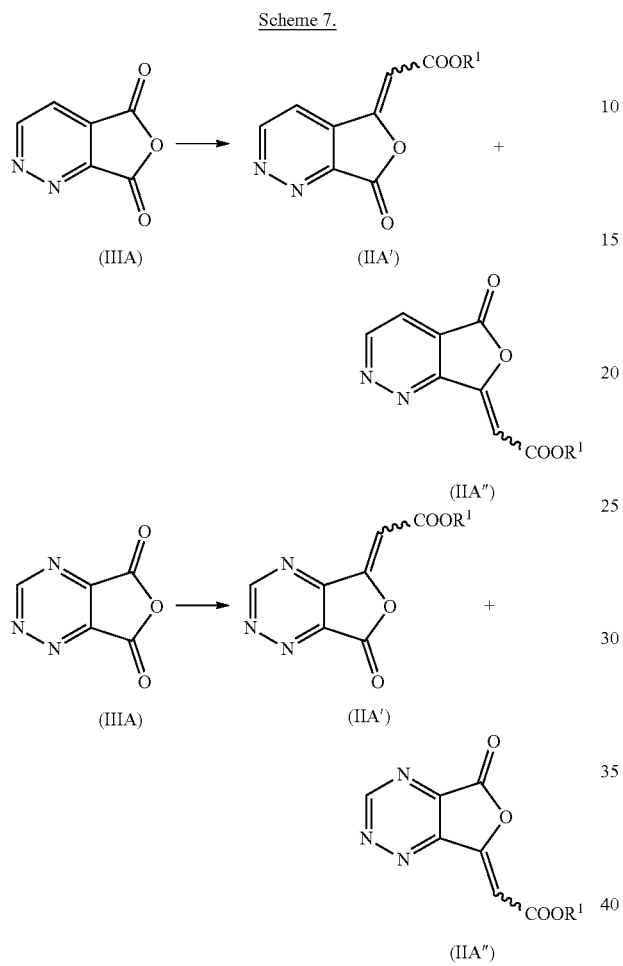

The compounds of Formula (IIIA) can generally be obtained through commercial sources, such as Sigma-Aldrich. Alternatively, compounds of Formula (IIIA) can be obtained reaction of dicarboxylic acid derivative represented by Formula (IVA) with a suitable anhydride forming reagent, such as dicyclohexylcarbodiimide (DCC) or acetic anhydride, to obtain the compounds of Formula (IIIA) as schematically illustrated below (Scheme 8). The reaction can be carried out using non-nucleophilic solvents, such as acetic anhydride, THF, and the like. The reaction can be carried out at temperatures of between about 20° C. to about 100° C., such as 60° C. to 80° C.

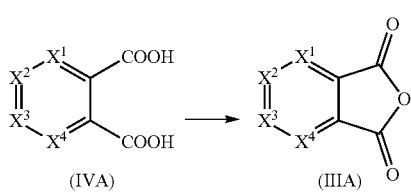

The compounds of Formula (IVA) can generally be obtained through commercial sources, such as Sigma-Aldrich. Alternatively, compounds of Formula (IVA) can be obtained reaction of suitable precursor represented by Formula (VA) with a suitable dicarboxylic acid derivative forming reagent, such as $NaMnO_4$ and/or NaOH, to obtain the compounds of Formula (IVA) as schematically illustrated below (Scheme 9). The reaction can be carried out using aqueous solvents, such as water. The reaction can be carried out at temperatures of between about 50° C. to about 100° C., such as 85° C. to 95° C.

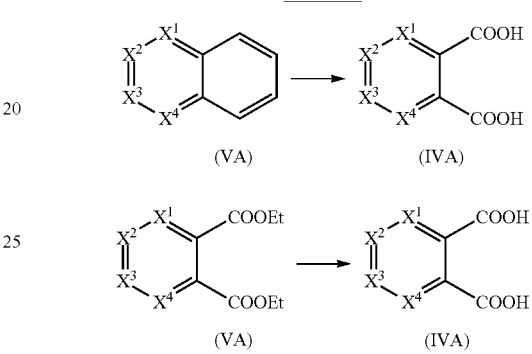

Additional Synthetic Schemes for Compound of Formula (I)

Additional reactions can be carried out for the synthesis of additional embodiments of compounds represented by formula (I).

To obtain compounds of formula (I) where Y is C=S, the following synthesis can be carried out (Scheme 10).

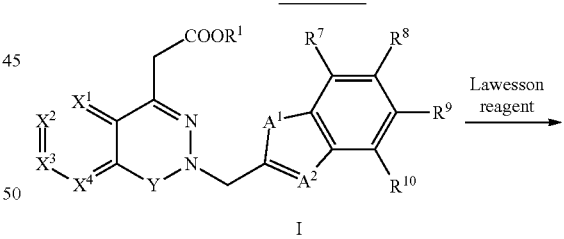

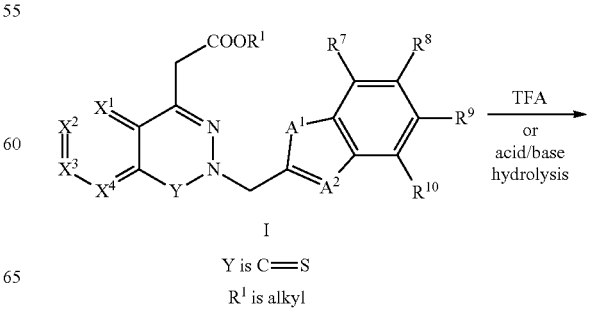

-continued

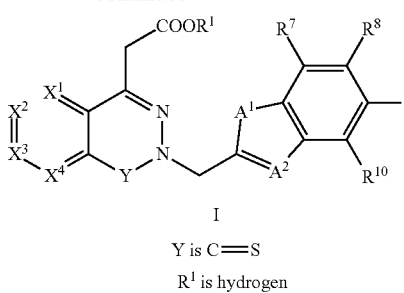

I
Y is C=S
R¹ is hydrogen

To obtain compounds of Formula (I) where Y is C=NR*, wherein R* represents hydrogen or an alkyl substituent for example, the following synthesis can be carried out (Scheme 11).

Scheme 11.

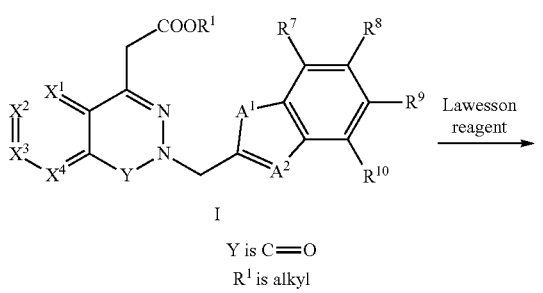

I
Y is C=O
R¹ is alkyl

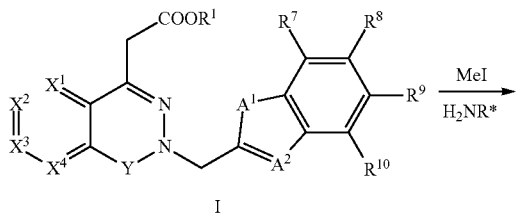

I
Y is C=S
R¹ is alkyl

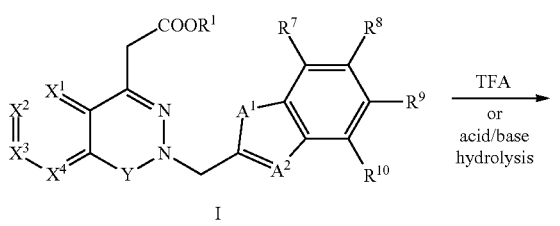

I
Y is C=NR*
R¹ is alkyl

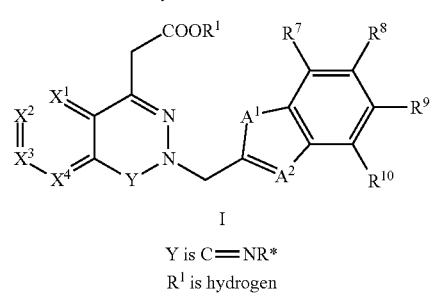

I
Y is C=NR*
R¹ is hydrogen

Alternative reaction schemes may be possible. For example, the following synthetic scheme may be carried out to obtain compounds of formula (I) where Y is a covalent bond (Scheme 12).

Scheme 12.

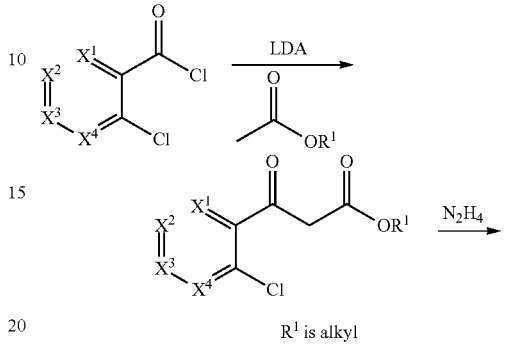

R¹ is alkyl

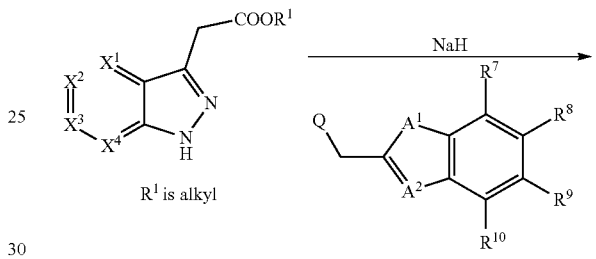

R¹ is alkyl

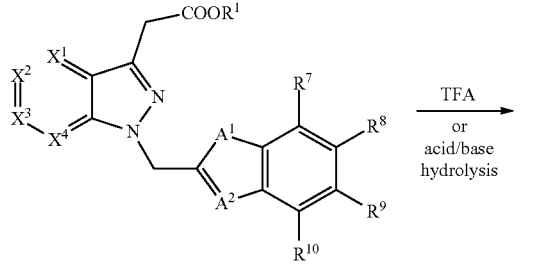

IB
R¹ is alkyl

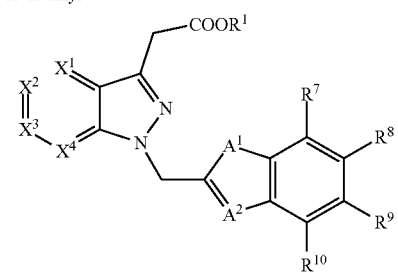

R¹ is hydrogen

In certain other embodiments, other types of reactions, such as the Perkins reaction, can be carried out to obtain compounds of formula (I) (Scheme 13). The Perkins reaction is shown illustrated below employing KOAc/Ac₂O. However, other temperatures and other bases, such as K₂CO₃ and the like can be utilized.

Other substitutions and modifications are further possible as would be apparent to one of ordinary skill in the art. For example, in Scheme 13, KOH can be utilized in place of NaOH. In Scheme 14 below, KO$^t$Bu can be used in place of NaH. Additionally, instead of DMF, NMP or THF can be utilized. Additional details of the Perkins reaction can be found in WO 03/061660, the contents of which are incorporated by reference herein in its entirety.

Scheme 13.

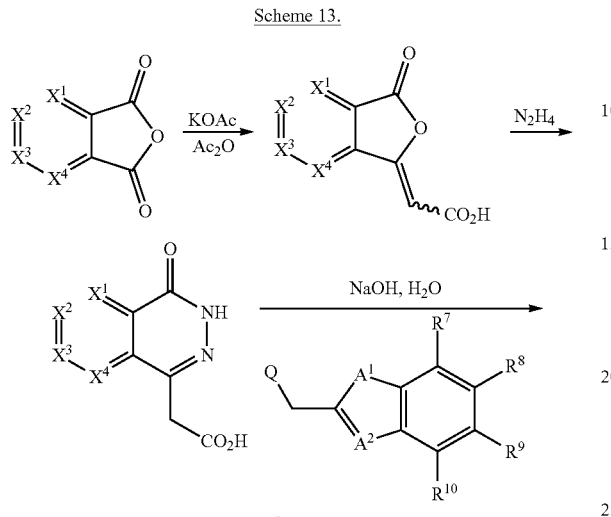

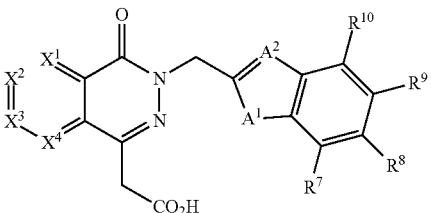

Scheme 14.

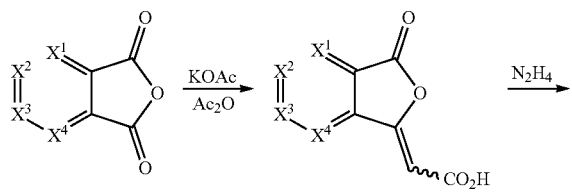

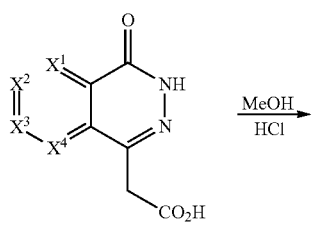

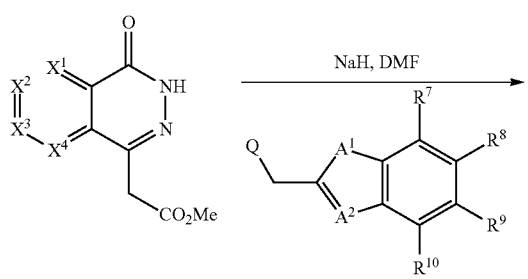

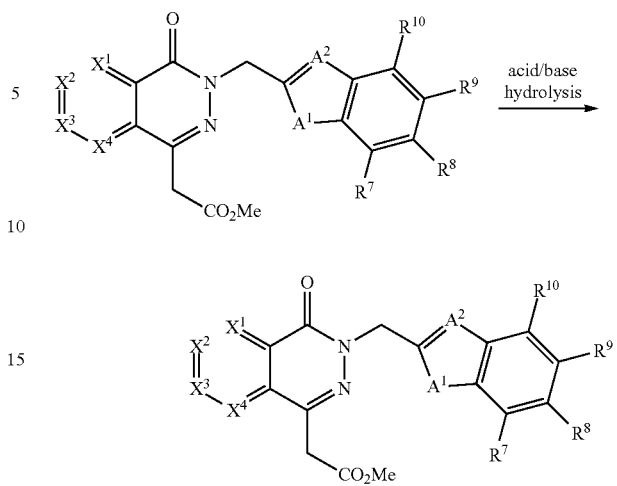

In certain embodiments, the following alternative synthesis can be carried out (Scheme 15).

Scheme 15.

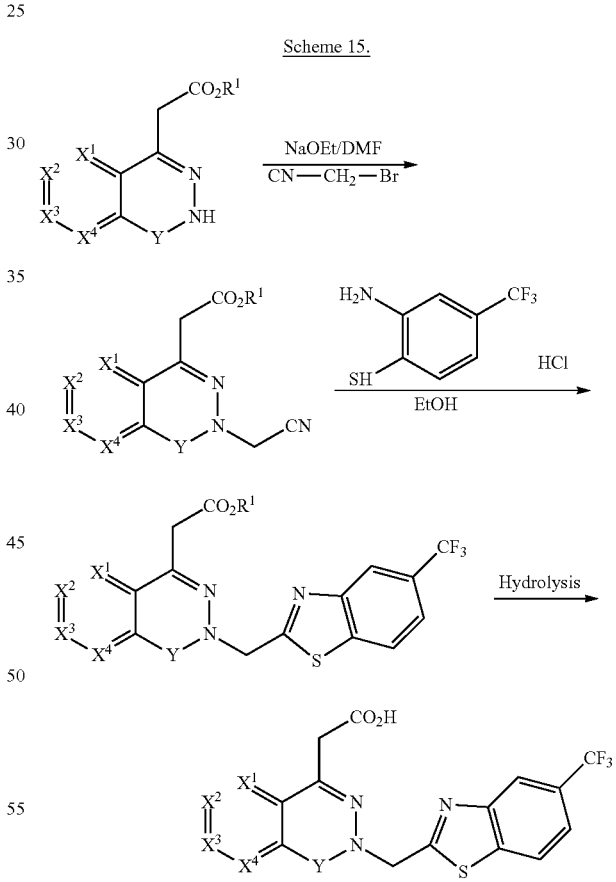

Exemplary Reaction Schemes to Produce Embodiments of Compounds of Formula (I)

Particular, non-limiting, illustrative synthetic schemes for certain embodiments are shown as follows.

Compounds of formula (I) where three of $X^1$, $X^2$, $X^3$, and $X^4$ are nitrogen and Y is C=O may be synthesized, for example, according to general Scheme 16.

Scheme 16.
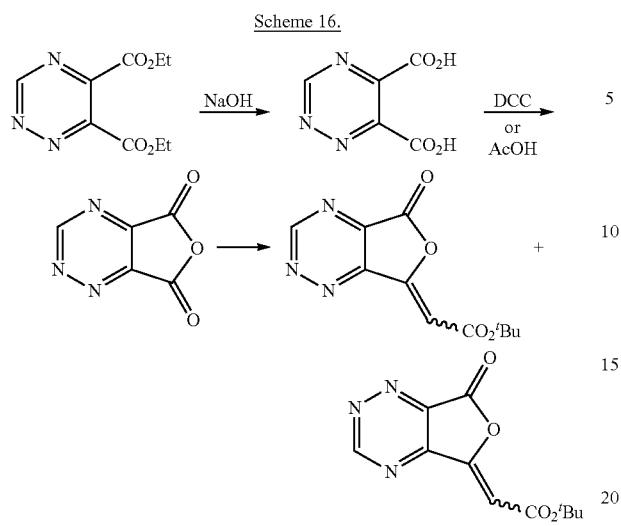
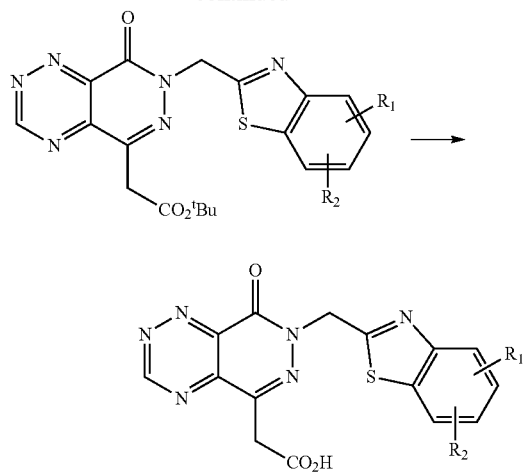
Compounds of formula (I) where $X^1$ and $X^4$ are nitrogen and Y is C=O may be synthesized, for example, according to general Scheme 17.
Scheme 17.
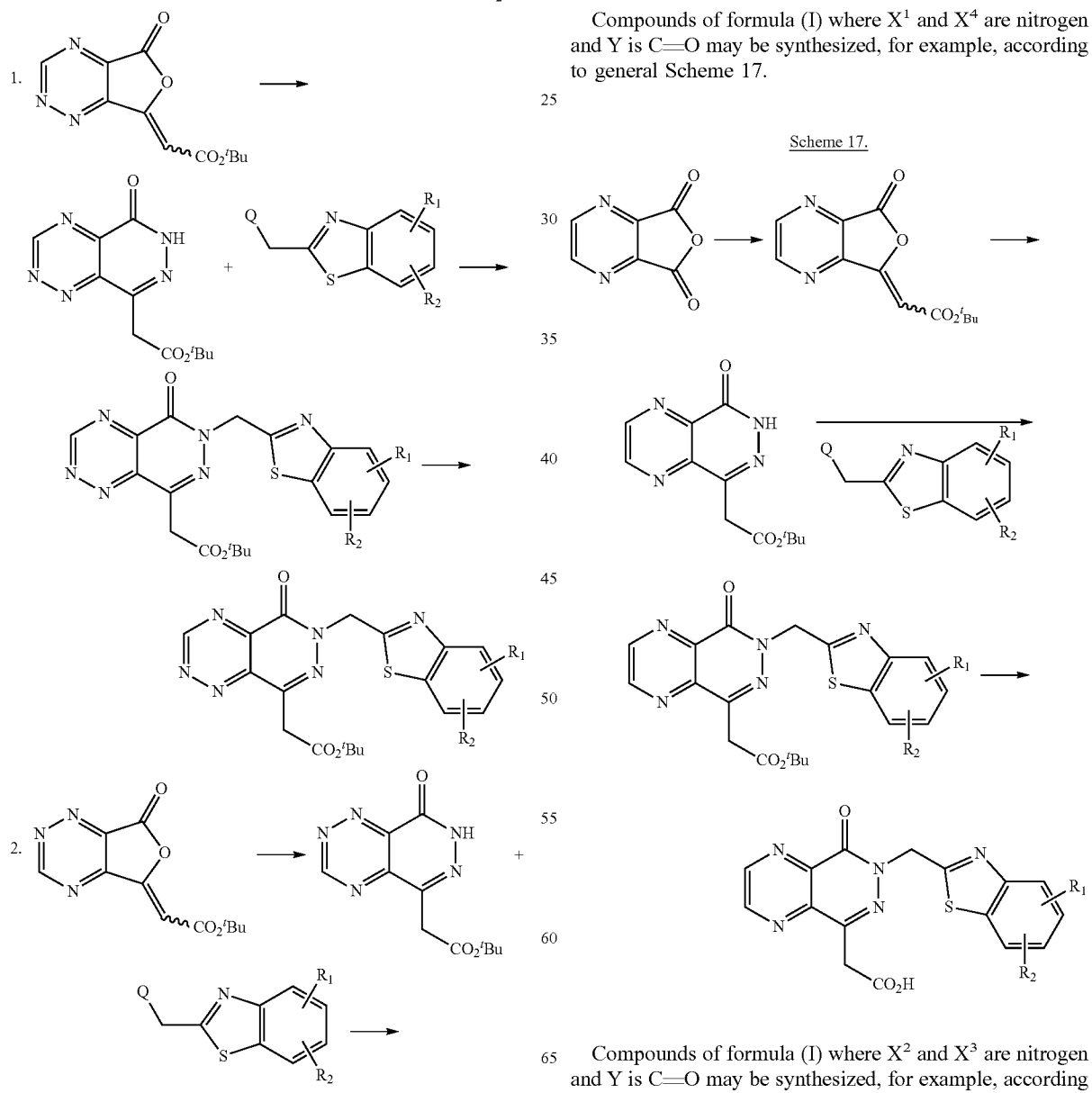
Compounds of formula (I) where $X^2$ and $X^3$ are nitrogen and Y is C=O may be synthesized, for example, according to general Scheme 18.

Scheme 18.
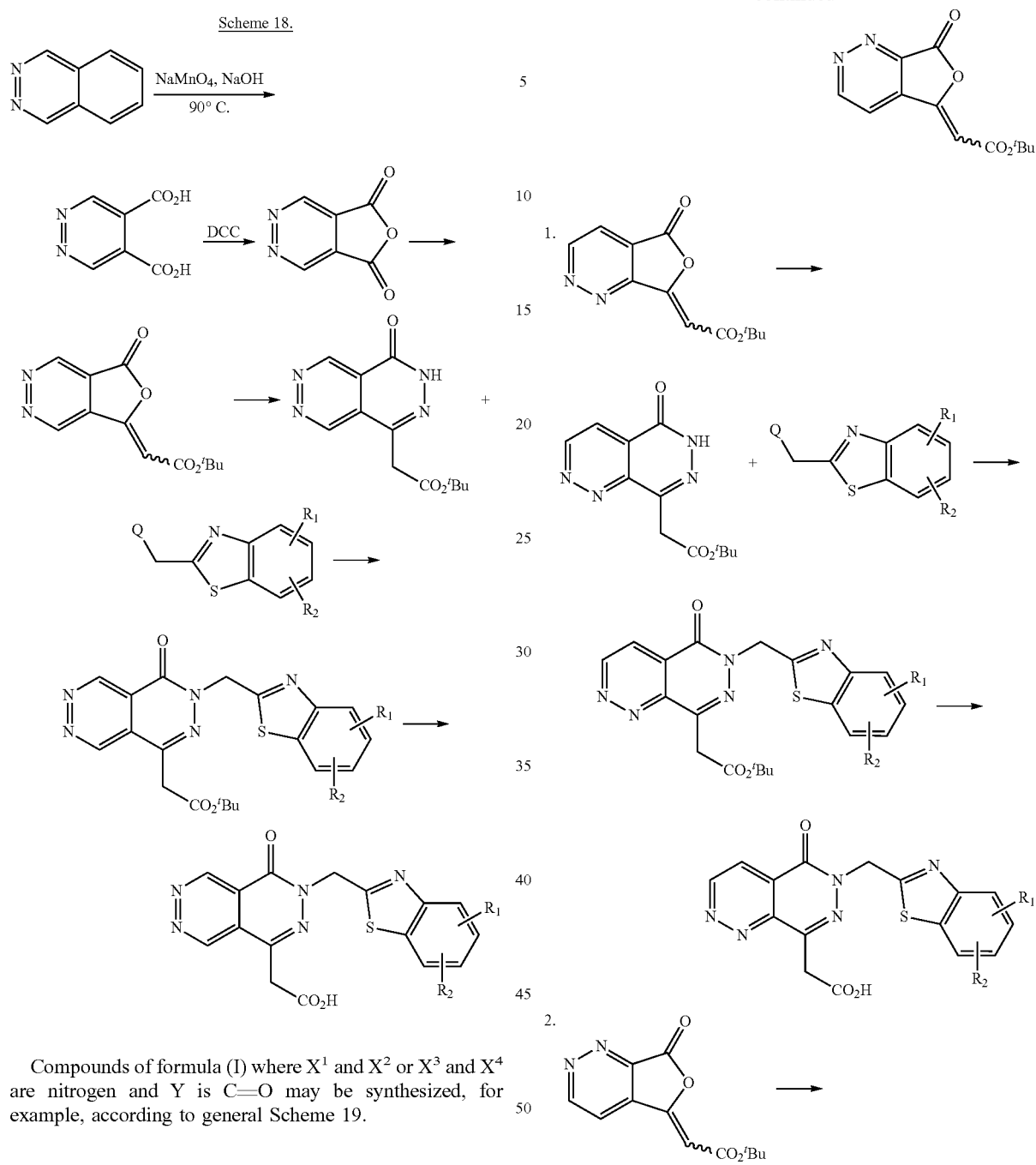
Compounds of formula (I) where $X^1$ and $X^2$ or $X^3$ and $X^4$ are nitrogen and Y is C=O may be synthesized, for example, according to general Scheme 19.
Scheme 19.
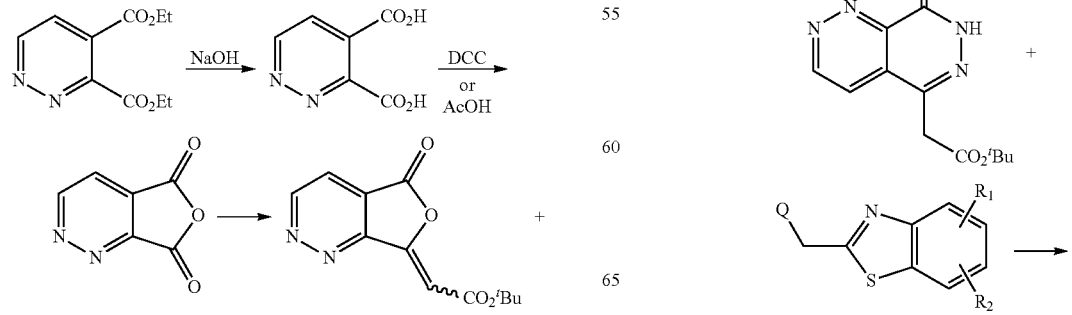

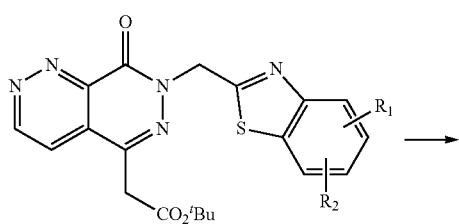
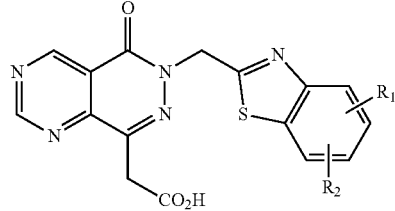

Compounds of formula (I) where $X^1$ and $X^3$ or $X^2$ and $X^4$ are nitrogen and Y is C=O may be synthesized, for example, according to general Scheme 20.

Scheme 20.

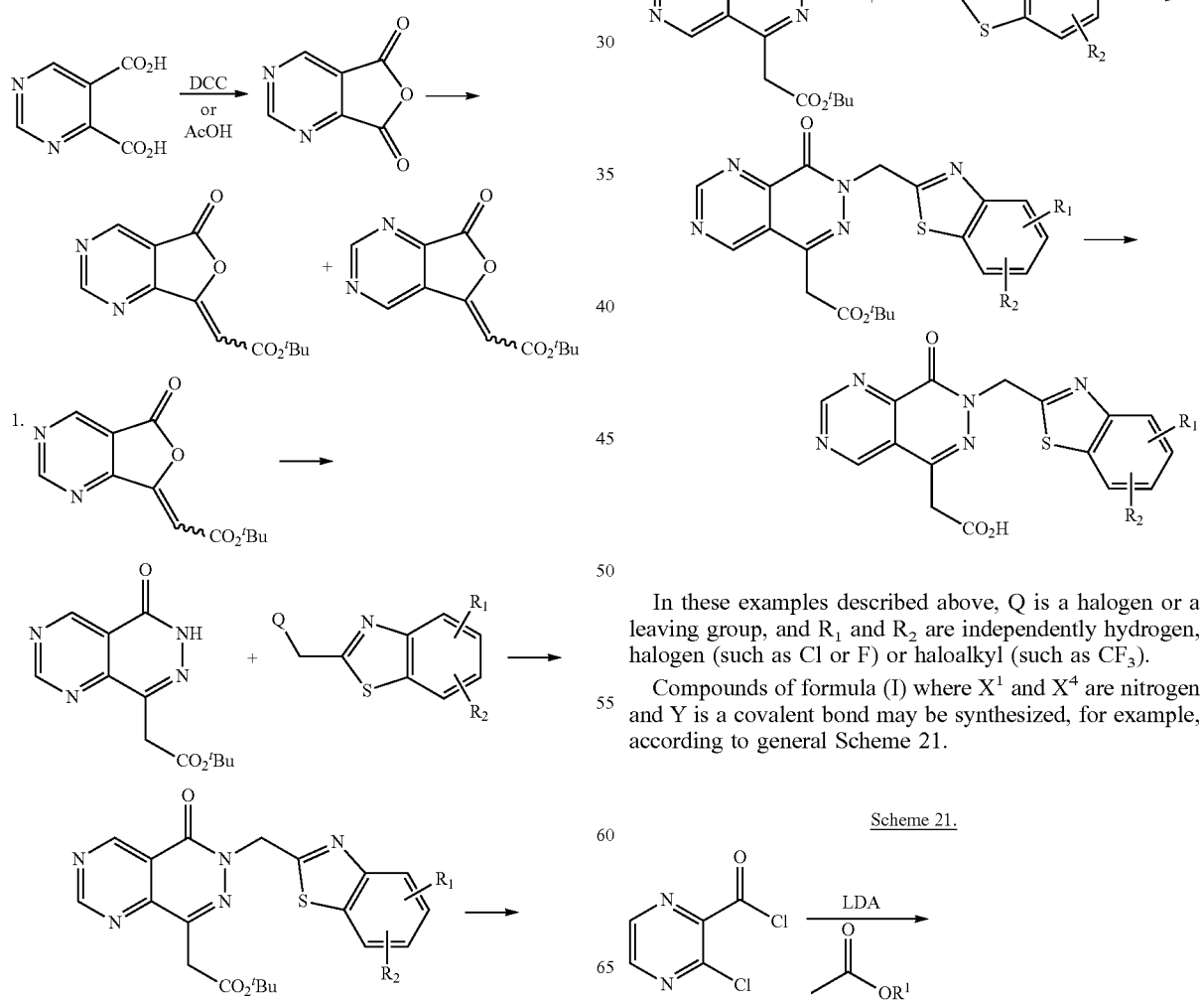

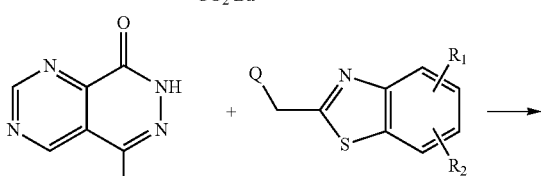

In these examples described above, Q is a halogen or a leaving group, and $R_1$ and $R_2$ are independently hydrogen, halogen (such as Cl or F) or haloalkyl (such as $CF_3$).

Compounds of formula (I) where $X^1$ and $X^4$ are nitrogen and Y is a covalent bond may be synthesized, for example, according to general Scheme 21.

Scheme 21.

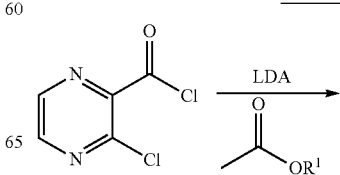

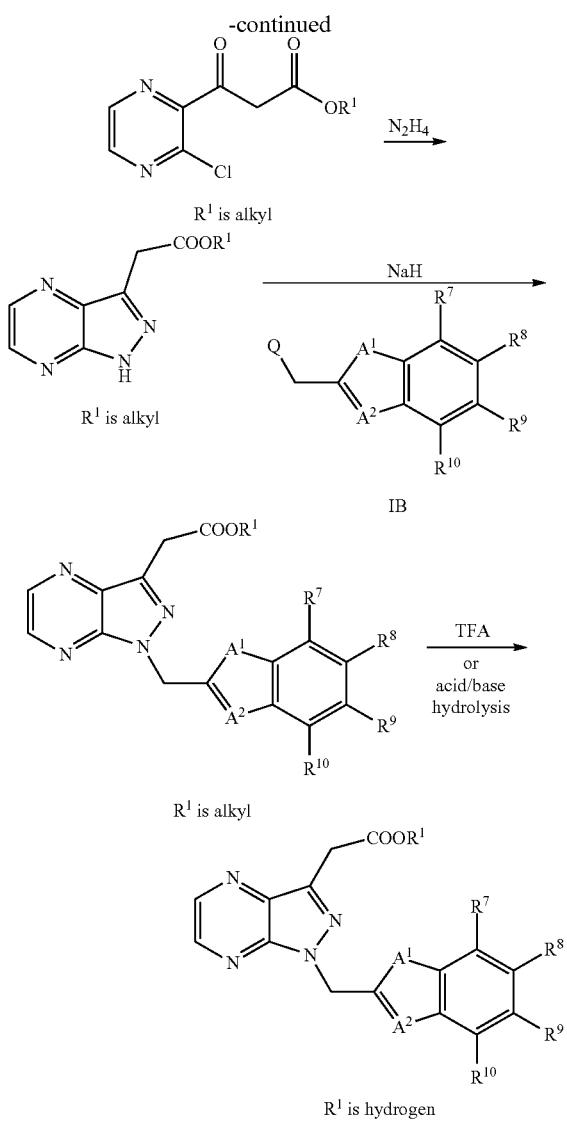

In the examples described above, the substituents are as described previously herein.

Compounds or compositions of the invention can be useful in applications that benefit from inhibition of aldose reductase enzymes. Exemplary utility of aldose reductase inhibition may be found, for example, in U.S. Pat. Nos. 5,677,342; 5,155,259; 4,939,140; U.S. patent application Ser. No. 11/210,283; and Roy et al., in Diabetes Research and Clinical Practice, Vol. 10, Issue 1, 91-97; and references cited therein; each of which hereby incorporated by reference in its entirety Inhibition of aldose reductase also has been found to prevent metastasis of colon cancer and mitosis in colon cancer cells (See, for example, Tammali, R. et al., Inhibition of Aldose Reductase Prevents Colon Cancer Metastasis, *Carcinogenesis* 2011, doi: 10.1093/carcin/bgr102; published online: Jun. 3, 2011; *Angiogenesis* 2011 May; 14(2):209-21; and *Mol. Cancer Ther.* 2010, April; 9(4): 813-824; each of which hereby incorporated by reference in its entirety).

In certain embodiments, compounds and/or compositions of the invention can be useful in promoting healthy aging of skin, the treatment of skin disorders, the treatment of angiogenesis disorders such as cancers, including colon cancer, the treatment of non-cardiac tissue damage, the treatment of cardiovascular disorders, the treatment of renal disorders, the treatment of evolving myocardial infarction, and the treatment various other disorders, such as complications arising from diabetes. Such disorders can include, but are not limited to, atherosclerosis, coronary artery disease, diabetic nephropathy, diabetic neuropathy, diabetic retinopathy, infections of the skin, peripheral vascular disease, stroke, and the like.

In certain embodiments, compounds and/or compositions of the invention can be useful in cardiovascular applications. For example, compounds and/or compositions of the invention can be used to treat patients undergoing a heart bypass surgery to improve recovery after the surgery. In another example, compounds and/or compositions of the invention can be used to inhibit or reduce accumulation or rapid onset of atherosclerotic plaque.

In some other embodiments, compounds and/or compositions of the invention can be useful in topical applications. For example, compounds and/or compositions of the invention can be used to retard or reduce skin aging.

In certain embodiments, compounds of formula (I) can be administered to a subject in need of treatment at dosages ranging from about 0.5 to about 25 mg/kg body weight of the subject to be treated per day, such as from about 1.0 to 10 mg/kg. However, additional variations are within the scope of the invention.

The compound of formula (I) can be administered alone or in combination with pharmaceutically acceptable carriers, such as diluents, fillers, aqueous solution, and even organic solvents. The compound and/or compositions of the invention can be administered as a tablet, powder, lozenge, syrup, injectable solution, and the like. Additional ingredients, such as flavoring, binder, excipients, and the like are within the scope of the invention.

In certain embodiments, pharmaceutically acceptable compositions can contain a compound of formula (I) and/or a pharmaceutically acceptable salt thereof at a concentration ranging from about 0.01 to about 2 wt %, such as 0.01 to about 1 wt % or about 0.05 to about 0.5 wt %. The composition can be formulated as a solution, suspension, ointment, or a capsule, and the like. The pharmaceutical composition can be prepared as an aqueous solution and can contain additional components, such as preservatives, buffers, tonicity agents, antioxidants, stabilizers, viscosity-modifying ingredients and the like.

Other equivalent modes of administration can be found in U.S. Pat. No. 4,939,140, hereby incorporated by reference herein in its entirety.

In one embodiment, the present invention provides for the use of pharmaceutical compositions and/or medicaments comprised of a compound of formula I, or a pharmaceutically acceptable salt, hydrate, solvate, or pro-drug thereof, in a method of treating a disease state, and/or condition caused by or related to aldose reductase.

In another embodiment, the method of treatment comprises the steps of: i) identifying a subject in need of such treatment; (ii) providing a compound of formula I, or a pharmaceutically acceptable salt, hydrate, solvate, pro-drug or tautomer thereof; and (iii) administering said compound of formula I in a therapeutically effective amount to treat, suppress and/or prevent the disease state or condition in a subject in need of such treatment.

In another embodiment, the method of treatment comprises the steps of: i) identifying a subject in need of such treatment; (ii) providing a composition comprising a compound of formula I, or a pharmaceutically acceptable salt, hydrate, solvate, pro-drug or tautomer thereof; and (iii) administering said composition in a therapeutically effective amount to treat, suppress and/or prevent the disease state or condition in a subject in need of such treatment.

In one embodiment, the compound or composition is administered orally.

In one embodiment, the methods comprise administering to the subject an effective amount of a compound of formula I, or a pharmaceutically acceptable salt, solvate, hydrate or pro-drug thereof; or a composition comprising a compound of formula I, or a pharmaceutically acceptable salt, solvate, hydrate or pro-drug thereof, and a pharmaceutically acceptable carrier. The pharmaceutically acceptable carriers are well-known to those skilled in the art, and include, for example, adjuvants, diluents, excipients, fillers, lubricants and vehicles. Often, the pharmaceutically acceptable carrier is chemically inert toward the active compounds and is non-toxic under the conditions of use. Examples of pharmaceutically acceptable carriers may include, for example, water or saline solution, polymers such as polyethylene glycol, carbohydrates and derivatives thereof, oils, fatty acids, or alcohols.

In another embodiment, the method of treatment, prevention and/or suppression of a condition related to aldose reductase comprises the steps of: i) identifying a subject in need of such treatment; (ii) providing a compound of formula I, or a pharmaceutically acceptable salt, solvate, hydrate or pro-drug thereof; or a composition comprising a compound of formula I, or a pharmaceutically acceptable salt, solvate, hydrate or pro-drug thereof, and a pharmaceutically acceptable carrier; and (iii) administering said compound or composition in a therapeutically effective amount to treat, prevent and/or suppress the disease state or condition related to aldose reductase in a subject in need of such treatment.

In one embodiment, the present invention also encompasses methods comprising pro-drugs of compounds of formula I and/or pharmaceutical compositions thereof. Pro-drugs include derivatives of compounds that can hydrolyze, oxidize, or otherwise react under biological conditions (in vitro or in vivo) to provide an active compound of the invention. Examples of pro-drugs include, but are not limited to, derivatives and metabolites of a compound of the invention that include biohydrolyzable moieties such as biohydrolyzable amides, biohydrolyzable esters, biohydrolyzable carbamates, biohydrolyzable carbonates, and biohydrolyzable phosphate analogues. Pro-drugs are also described in, for example, *The Practice of Medicinal Chemistry* (Camille Wermuth, ed., 1999, Academic Press; hereby incorporated by reference in its entirety). In certain embodiments, pro-drugs of compounds with carboxyl functional groups are the lower alkyl esters of the carboxylic acid. The carboxylate esters are conveniently formed by esterifying any of the carboxylic acid moieties present on the molecule. Pro-drugs can typically be prepared using well-known methods, such as those described by *Burger's Medicinal Chemistry and Drug Discovery* 6$^{th}$ ed. (Donald J. Abraham ed., 2001, Wiley) and *Design and Application of Pro-drugs* (H. Bundgaard ed., 1985, Harwood Academic Publishers Gmfh; each of which hereby incorporated by reference in its entirety). Biohydrolyzable moieties of a compound of formula I 1) do not interfere with the biological activity of the compound but can confer upon that compound advantageous properties in vivo, such as uptake, duration of action, or onset of action; or 2) may be biologically inactive but are converted in vivo to the biologically active compound. Examples of biohydrolyzable esters include, but are not limited to, lower alkyl esters, alkoxyacyloxy esters, alkyl acylamino alkyl esters, and choline esters. Examples of biohydrolyzable amides include, but are not limited to, lower alkyl amides, α-amino acid amides, alkoxyacyl amides, and alkylaminoalkylcarbonyl amides. Examples of biohydrolyzable carbamates include, but are not limited to, lower alkylamines, substituted ethylenediamines, aminoacids, hydroxyalkylamines, heterocyclic and heteroaromatic amines, and polyether amines In one embodiment, the compounds of the invention are formulated into pharmaceutical compositions for administration to subjects in a biologically compatible form suitable for administration in vivo. According to another aspect, the present invention provides a pharmaceutical composition comprising a compound of formula I in admixture with a pharmaceutically acceptable diluent and/or carrier. The pharmaceutically-acceptable carrier is "acceptable" in the sense of being compatible with the other ingredients of the composition and not deleterious to the recipient thereof. The pharmaceutically-acceptable carriers employed herein may be selected from various organic or inorganic materials that are used as materials for pharmaceutical formulations and which are incorporated as analgesic agents, buffers, binders, disintegrants, diluents, emulsifiers, excipients, extenders, glidants, solubilizers, stabilizers, suspending agents, tonicity agents, vehicles and viscosity-increasing agents. Pharmaceutical additives, such as antioxidants, aromatics, colorants, flavor-improving agents, preservatives, and sweeteners, may also be added. Examples of acceptable pharmaceutical carriers include carboxymethyl cellulose, crystalline cellulose, glycerin, gum arabic, lactose, magnesium stearate, methyl cellulose, powders, saline, sodium alginate, sucrose, starch, talc and water, among others. In one embodiment, the term "pharmaceutically acceptable" means approved by a regulatory agency of the Federal or a state government or listed in the U.S. Pharmacopeia or other generally recognized pharmacopeia for use in animals, and more particularly in humans.

Surfactants such as, for example, detergents, are also suitable for use in the formulations. Specific examples of surfactants include polyvinylpyrrolidone, polyvinyl alcohols, copolymers of vinyl acetate and of vinylpyrrolidone, polyethylene glycols, benzyl alcohol, mannitol, glycerol, sorbitol or polyoxyethylenated esters of sorbitan; lecithin or sodium carboxymethylcellulose; or acrylic derivatives, such as methacrylates and others, anionic surfactants, such as alkaline stearates, in particular sodium, potassium or ammonium stearate; calcium stearate or triethanolamine stearate; alkyl sulfates, in particular sodium lauryl sufate and sodium cetyl sulfate; sodium dodecylbenzenesulphonate or sodium dioctyl sulphosuccinate; or fatty acids, in particular those derived from coconut oil, cationic surfactants, such as water-soluble quaternary ammonium salts of formula $N^+R'R''R'''R''''Y^-$, in which the R radicals are identical or different optionally hydroxylated hydrocarbon radicals and $Y^-$ is an anion of a strong acid, such as halide, sulfate and sulfonate anions; cetyltrimethylammonium bromide is one of the cationic surfactants which can be used, amine salts of formula $N^+R'R''R'''$, in which the R radicals are identical or different optionally hydroxylated hydrocarbon radicals; octadecylamine hydrochloride is one of the cationic surfactants which can be used, non-ionic surfactants, such as optionally polyoxyethylenated esters of sorbitan, in particular Polysorbate 80, or polyoxyethylenated alkyl ethers; polyethylene glycol stearate, polyoxyethylenated derivatives of castor oil, polyglycerol esters, polyoxyethylenated fatty alcohols, polyoxyethylenated fatty acids or copolymers of ethylene oxide and of propylene oxide, amphoteric surfactants, such as substituted lauryl compounds of betaine, When administered to a subject, the compound of formula I and pharmaceutically acceptable carriers can be sterile. Suitable pharmaceutical carriers may also include excipients such as starch, glucose, lactose, sucrose, gelatin, malt, rice, flour, chalk, silica gel, sodium stearate, glycerol monostearate, talc, sodium chloride, dried skim milk, glycerol, propylene, glycol, polyethylene glycol 300, water, ethanol, polysorbate 20, and the like. The present compositions, if desired, may also contain minor amounts of wetting or emulsifying agents, or pH buffering agents.

The pharmaceutical formulations of the present invention are prepared by methods well-known in the pharmaceutical arts. Optionally, one or more accessory ingredients (e.g., buffers, flavoring agents, surface active agents, and the like) also are added. The choice of carrier is determined by the solubility and chemical nature of the compounds, chosen route of administration and standard pharmaceutical practice.

Additionally, the compounds and/or compositions of the present invention are administered to a human or animal subject by known procedures including oral administration, sublingual or buccal administration. In one embodiment, the compound and/or composition is administered orally.

For oral administration, a formulation of the compounds of the invention may be presented in dosage forms such as capsules, tablets, powders, granules, or as a suspension or solution. Capsule formulations may be gelatin, soft-gel or solid. Tablets and capsule formulations may further contain one or more adjuvants, binders, diluents, disintegrants, excipients, fillers, or lubricants, each of which are known in the art. Examples of such include carbohydrates such as lactose or sucrose, dibasic calcium phosphate anhydrous, corn starch, mannitol, xylitol, cellulose or derivatives thereof, microcrystalline cellulose, gelatin, stearates, silicon dioxide, talc, sodium starch glycolate, acacia, flavoring agents, preservatives, buffering agents, disintegrants, and colorants. Orally administered compositions may contain one or more optional agents such as, for example, sweetening agents such as fructose, aspartame or saccharin; flavoring agents such as peppermint, oil of wintergreen, or cherry; coloring agents; and preservative agents, to provide a pharmaceutically palatable preparation.

In some embodiments, the composition is in unit dose form such as a tablet, capsule or single-dose vial. Suitable unit doses, i.e., therapeutically effective amounts, may be determined during clinical trials designed appropriately for each of the conditions for which administration of a chosen compound is indicated and will, of course, vary depending on the desired clinical endpoint.

In accordance with the methods of the present invention, the compounds of the invention are administered to the subject in a therapeutically effective amount, for example to reduce or ameliorate symptoms related to aldose reductase activity in the subject. This amount is readily determined by the skilled artisan, based upon known procedures, including analysis of titration curves established in vivo and methods and assays disclosed herein.

In one embodiment, the methods comprise administration of a therapeutically effective dosage of the compounds of the invention. In some embodiments, the therapeutically effective dosage is at least about 0.05 mg/kg body weight, at least about 0.1 mg/kg body weight, at least about 0.25 mg/kg body weight, at least about 0.3 mg/kg body weight, at least about 0.5 mg/kg body weight, at least about 0.75 mg/kg body weight, at least about 1 mg/kg body weight, at least about 2 mg/kg body weight, at least about 3 mg/kg body weight, at least about 4 mg/kg body weight, at least about 5 mg/kg body weight, at least about 6 mg/kg body weight, at least about 7 mg/kg body weight, at least about 8 mg/kg body weight, at least about 9 mg/kg body weight, at least about 10 mg/kg body weight, at least about 15 mg/kg body weight, at least about 20 mg/kg body weight, at least about 25 mg/kg body weight, at least about 30 mg/kg body weight, at least about 40 mg/kg body weight, at least about 50 mg/kg body weight, at least about 75 mg/kg body weight, at least about 100 mg/kg body weight, at least about 200 mg/kg body weight, at least about 250 mg/kg body weight, at least about 300 mg/kg body weight, at least about 350 mg/kg body weight, at least about 400 mg/kg body weight, at least about 450 mg/kg body weight, at least about 500 mg/kg body weight, at least about 550 mg/kg body weight, at least about 600 mg/kg body weight, at least about 650 mg/kg body weight, at least about 700 mg/kg body weight, at least about 750 mg/kg body weight, at least about 800 mg/kg body weight, at least about 900 mg/kg body weight, or at least about 1000 mg/kg body weight. It will be recognized that any of the dosages listed herein may constitute an upper or lower dosage range, and may be combined with any other dosage to constitute a dosage range comprising an upper and lower limit.

In some embodiments, the methods comprise a single dosage or administration (e.g., as a single injection or deposition). Alternatively, the methods comprise administration once daily, twice daily, three times daily or four times daily to a subject in need thereof for a period of from about 2 to about 28 days, or from about 7 to about 10 days, or from about 7 to about 15 days, or longer. In some embodiments, the methods comprise chronic administration. In yet other embodiments, the methods comprise administration over the course of several weeks, months, years or decades. In still other embodiments, the methods comprise administration over the course of several weeks. In still other embodiments, the methods comprise administration over the course of several months. In still other embodiments, the methods comprise administration over the course of several years. In still other embodiments, the methods comprise administration over the course of several decades.

The dosage administered can vary depending upon known factors such as the pharmacodynamic characteristics of the active ingredient and its mode and route of administration; time of administration of active ingredient; age, sex, health and weight of the recipient; nature and extent of symptoms; kind of concurrent treatment, frequency of treatment and the effect desired; and rate of excretion. These are all readily determined and may be used by the skilled artisan to adjust or titrate dosages and/or dosing regimens.

The precise dose to be employed in the compositions will also depend on the route of administration, and should be decided according to the judgment of the practitioner and each patient's circumstances. In specific embodiments of the invention, suitable dose ranges for oral administration of the compounds of the invention are generally about 1 mg/day to about 1000 mg/day. In one embodiment, the oral dose is about 1 mg/day to about 800 mg/day. In one embodiment, the oral dose is about 1 mg/day to about 500 mg/day. In another embodiment, the oral dose is about 1 mg/day to about 250 mg/day. In another embodiment, the oral dose is about 1 mg/day to about 100 mg/day. In another embodiment, the oral dose is about 5 mg/day to about 50 mg/day. In another embodiment, the oral dose is about 5 mg/day. In another embodiment, the oral dose is about 10 mg/day. In another embodiment, the oral dose is about 20 mg/day. In another embodiment, the oral dose is about 30 mg/day. In another embodiment, the oral dose is about 40 mg/day. In another embodiment, the oral dose is about 50 mg/day. In another embodiment, the oral dose is about 60 mg/day. In another embodiment, the oral dose is about 70 mg/day. In another embodiment, the oral dose is about 100 mg/day. It will be recognized that any of the dosages listed herein may constitute an upper or lower dosage range, and may be combined with any other dosage to constitute a dosage range comprising an upper and lower limit.

Any of the compounds and/or compositions of the invention may be provided in a kit comprising the compounds and/or compositions. Thus, in one embodiment, the compound and/or composition of the invention is provided in a kit.

Those skilled in the art will recognize, or be able to ascertain using no more than routine experimentation, many equivalents to the specific embodiments of the invention described herein. Such equivalents are intended to be within the scope of the present invention.

The invention is further described by the following non-limiting Examples.

EXAMPLES

Examples are provided below to facilitate a more complete understanding of the invention. The following examples serve to illustrate the exemplary modes of making and practicing the invention. However, the scope of the invention is not to be construed as limited to specific embodiments disclosed in these Examples, which are illustrative only.

Example 1

Preparation of Compound A

Compound A was prepared as schematically illustrated below.

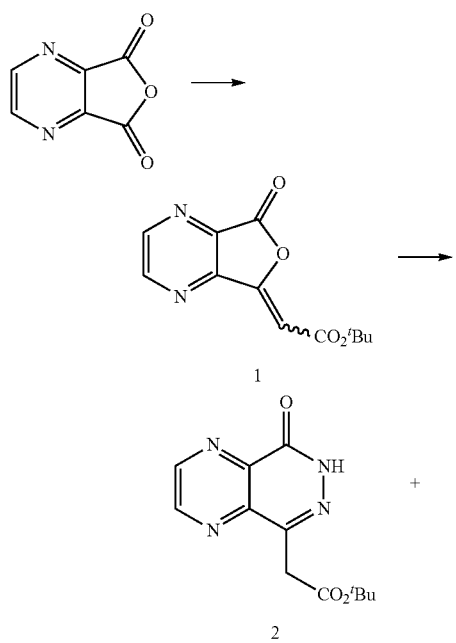

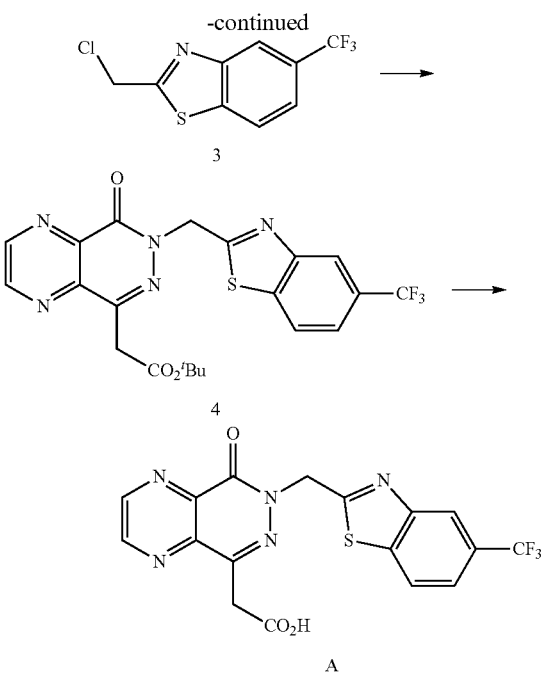

Preparation of (E)/(Z)-tert-butyl 2-(7-oxofuro[3,4-b]pyrazin-5(7H)-ylidene)acetate (Compound 1)

To a stirred solution of 5.05 g (33.63 mmol) of commercially available 2,3-pyrazinedicarboxylic anhydride in 300 mL of $CHCl_3$ was added 12.34 g (33.63 mmol) of (tert-butoxycarbonylmethylene)-triphenylphosphorane. The resulting solution was heated to 62° C. for 2 days. The reaction mixture was concentrated in vacuo and the residue purified via flash column chromatography over silica gel (monitored by thin layer chromatography) and eluted with 1:1 (v/v) hexanes:ethyl acetate. Evaporation of the collected fractions yielded 2.99 g (36% yield) of (E)/(Z)-tert-butyl 2-(7-oxofuro[3,4-b]pyrazin-5(7H)-ylidene)acetate (Compound 1) as a mixture of geometrical isomers (~1:1) that was not separated: $^1$H NMR ($CDCl_3$, 300 MHz): $\delta_{ppm}$ 9.03 (d, J=2.4 Hz, 1H), 8.96 (d, J=2.4 Hz, 1H), 8.92 (d, J=2.4 Hz, 1H), 8.90 (d, J=2.4 Hz, 1H), 6.32 (s, 2H), 1.58 (s, 18H).

Preparation of tert-butyl 2-(8-oxo-7,8-dihydropyrazino[2,3-d]pyridazin-5-yl)acetate (Compound 2)

To a stirred solution of 9.42 g (37.99 mmol) of (E)/(Z)-tert-butyl 2-(7-oxofuro[3,4-b]pyrazin-5(7H)-ylidene)acetate (Compound 1) in 600 mL of ethanol was added 1.25 mL (39.90 mmol) of hydrazine. The resulting solution was brought to 80° C. for 3 hours. Subsequently, the reaction mixture was concentrated in vacuo and the residue purified via flash column chromatography over silica gel (monitored by thin layer chromatography) and eluted with 19:1 (v/v) methylene chloride:methanol. Evaporation of the collected fractions yielded 7.78 g (78% yield) of tert-butyl 2-(8-oxo-7,8-dihydropyrazino[2,3-d]pyridazin-5-yl)acetate (Compound 2): $^1$H NMR ($CDCl_3$, 300 MHz): $\delta_{ppm}$ 10.67 (br s, 1H), 9.06 (d, J=2.1 Hz, 1H), 9.04 (d, J=2.1 Hz, 1H), 4.02 (s, 2H), 1.43 (s, 9H).

Preparation of tert-butyl 2-(8-oxo-7-((5-(trifluoromethyl)benzo[d]thiazol-2-yl)methyl)-7,8-dihydropyrazino[2,3-d]pyridazin-5-yl)acetate (Compound 4)

To a stirred solution of 7.78 g (29.58 mmol) of tert-butyl 2-(8-oxo-7,8-dihydropyrazino[2,3-d]pyridazin-5-yl)acetate (Compound 2) in 300 mL of DMF was added 3.49 g (31.06 mmol) of potassium tert-butoxide. The resulting reaction mixture was stirred at ambient temperature for 0.5 hours. Subsequently, a solution of 7.80 g (31.06 mmol) of 2-(chloromethyl)-5-(trifluoromethyl)benzo[d]thiazole (Compound 3) in 20 mL of DMF was added and the resulting reaction mixture stirred at ambient temperature overnight. The reaction mixture was then partitioned between ethyl acetate and water, the layers separated, and the ethyl acetate layer washed with a copious amount of water (3×). The organic layer was dried over $Na_2SO_4$, filtered and concentrated in vacuo. The residue was purified via flash column chromatography over silica gel (monitored by thin layer chromatography) and eluted with a gradient of 3:1 (v/v) hexanes: ethyl acetate to 1:1 (v/v) hexanes:ethyl acetate. The obtained residue was then rechromatographed over silica gel and eluted with 49:1 (v/v) methylene chloride:methanol. Evaporation of the collected fractions yielded 6.88 g (48% yield) of tert-butyl 2-(8-oxo-7-((5-(trifluoromethyl)benzo[d]thiazol-2-yl)methyl)-7,8-dihydropyrazino[2,3-d]pyridazin-5-yl)acetate (Compound 4): $^1$H NMR ($CDCl_3$, 300 MHz): $\delta_{ppm}$ 9.08 (d, J=2.1 Hz, 1H), 9.04 (d, J=2.1 Hz, 1H), 8.27 (s, 1H), 7.94 (d, J=8.4 Hz, 1H), 7.61 (d, J=8.4 Hz, 1H), 5.89 (s, 2H), 4.04 (s, 2H), 1.42 (s, 9H).

Preparation of 2-(8-oxo-7-((5-(trifluoromethyl) benzo[d]thiazol-2-yl)methyl)-7,8-dihydropyrazino[2, 3-d]pyridazin-5-yl)acetic acid (Compound A)

To a stirred solution of 6.0 g (12.55 mmol) of tert-butyl 2-(8-oxo-7-((5-(trifluoromethyl)benzo-[d]thiazol-2-yl) methyl)-7,8-dihydropyrazino[2,3-d]pyridazin-5-yl)acetate (Compound 4) in 41 mL of $CH_2Cl_2$ was added 82 mL of TFA. The resulting reaction mixture was stirred at ambient temperature for 1 hour. Subsequently, the reaction mixture was concentrated in vacuo and the residue partitioned between ethyl acetate and 1.0 M KOH in water. The layers were separated and the aqueous layer extracted with ethyl acetate (2×). The aqueous layer was acidified to a pH ~2 with concentrated HCl and subsequently extracted with ethyl acetate (3×). The organics from the second extraction were dried over $Na_2SO_4$, filtered and concentrated in vacuo. The residue was purified via flash column chromatography over silica gel (monitored by thin layer chromatography) and eluted with 19:1 (v/v) methylene chloride:methanol containing 1% (by volume) acetic acid. Evaporation of the collected fractions yielded 2.30 g (44% yield) of 2-(8-oxo-7-((5-(trifluoromethyl)benzo[d]thiazol-2-yl)methyl)-7,8-dihydropyrazino[2,3-d]pyridazin-5-yl)acetic acid (Compound A) as a solid: $^1$H NMR (DMSO-$d_6$, 300 MHz): $\delta_{ppm}$ 9.26 (d, J=2.1 Hz, 1H), 9.22 (d, J=2.1 Hz, 1H), 8.37 (s, 1H), 8.35 (d, J=8.4 Hz, 1H), 7.79 (d, J=8.4 Hz, 1H), 5.88 (s, 2H), 4.03 (s, 2H); m.p.=192-193° C.

Example 2

Alternate Preparation of Compound A

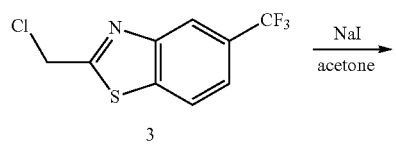

Preparation of 2-(iodomethyl)-5-(trifluoromethyl)benzo[d]thiazole (Compound 5)

To a stirred solution of 10.79 g (42.97 mmol) of 2-(chloromethyl)-5-(trifluoromethyl)benzo[d]thiazole (Compound 3) in 86 mL of acetone was added 7.40 g (49.42 mmol) of sodium iodide. The resulting reaction mixture was heated to 55° C. for 1 hour. The reaction mixture was cooled to ambient temperature and concentrated in vacuo. The residue

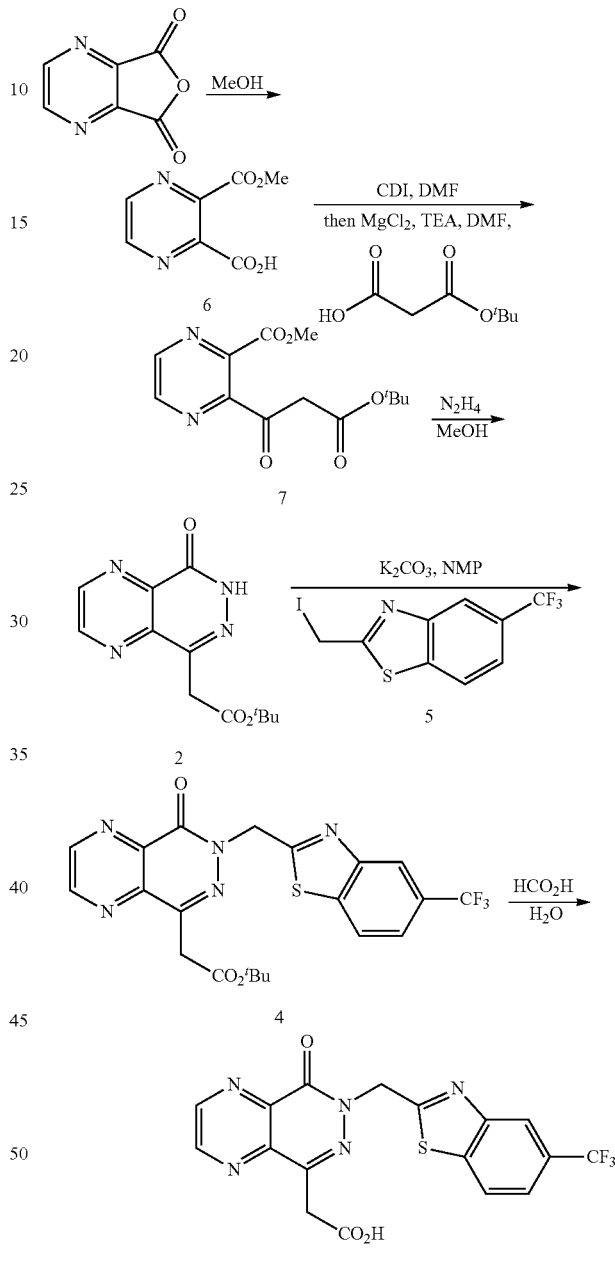

was partitioned between EtOAc and water, the layers separated, and the organic layer washed with water (1×). The recovered organic layer was then treated with 1.0 M $Na_2S_2O_3$ and stirred vigorously for 15 minutes. The layers were then separated and the organic layer washed sequentially with water (1×) and brine (1×). The organic layer was dried over $Na_2SO_4$, filtered and concentrated in vacuo to yield 14.28 g (97% crude yield) of 2-(iodomethyl)-5-(trifluoromethyl)benzo[d]thiazole (Compound 5) that was used without further purification: $^1$H NMR (CDCl$_3$, 300 MHz): $\delta_{ppm}$ 8.26 (s, 1H), 7.95 (d, J=8.4 Hz, 1H), 7.66 (d, J=8.4 Hz, 1H), 4.80 (s, 2H).

Preparation of
3-(methoxycarbonyl)pyrazine-2-carboxylic acid
(Compound 6)

A solution of 12.0 g (79.95 mmol) of 2,3-pyrazine dicarboxylic anhydride in 282 mL of MeOH was heated to 65° C. overnight. The reaction mixture was cooled to ambient temperature and concentrated in vacuo. To the obtained residue was added water followed by slow addition of solid $NaHCO_3$. After gas evolution ceased, the aqueous layer was extracted with EtOAc (1×). The aqueous layer was then acidified to pH 2 by addition of conc. HCl. The aqueous layer was extracted with EtOAc (2×) and the combined organics from the second extraction washed with brine (1×). The organic layer was dried over $Na_2SO_4$, filtered and concentrated in vacuo to yield 12.41 g (85% crude yield) of 3-(methoxycarbonyl)pyrazine-2-carboxylic acid (Compound 6) as a white powder that was used without further purification: $^1$H NMR (DMSO, 300 MHz): $\delta_{ppm}$ 8.91 (d, J=2.7 Hz, 1H), 8.89 (d, J=2.7 Hz, 1H), 3.91 (s, 3H).

Preparation of tert-butyl 2-(8-oxo-7,8-dihydropyrazino[2,3-d]pyridazin-5-yl)acetate (Compound 2)

In flask #1, a solution of 12.23 g (67.22 mmol) of 3-(methoxycarbonyl)pyrazine-2-carboxylic acid (Compound 6) in 88 mL of DMF was treated slowly with 12.53 g (77.28 mmol) of CDI. The reaction mixture was stirred at ambient temperature for 2 hours.
In a separate flask, flask #2, to 147 mL of DMF cooled to 0° C. was added portionwise 8.32 g (87.39 mmol) of $MgCl_2$. After stirring at 0° C. for 5 minutes, 13.5 mL (87.39 mmol) of mono-tert-butyl malonate and 37.4 mL (269 mmol) of triethylamine was added and the resulting reaction mixture stirred at ambient temperature for 2 hours. After 2 hours, the content of flask #1 was added to flask #2 and the combined reaction mixture stirred at ambient temperature overnight. Subsequently, the reaction mixture was poured into aqueous 1.0 M HCl cooled to 0° C. and stirred for 15 minutes. To the mixture was added Et$_2$O, the layers separated, and the ethereal layer washed sequentially with water (1×), saturated aqueous $NaHCO_3$ (1×), water (1×) and brine (1×). The organic organic layer was dried over $Na_2SO_4$, filtered and concentrated in vacuo to yield crude methyl 3-(3-(tert-butoxy)-3-oxopropanoyl)pyrazine-2-carboxylate (Compound 7) that was used without further purification.
The crude methyl 3-(3-(tert-butoxy)-3-oxopropanoyl) pyrazine-2-carboxylate (Compound 7) was taken up in 250 mL of MeOH and the resulting solution cooled to 0° C. Subsequently, 2.2 mL (70.58 mmol) of hydrazine was added in a drop-wise fashion and the reaction mixture was warmed to ambient temperature for 1 hour. After 1 hour, the reaction mixture was concentrated in vacuo and the residue purified via flash column chromatography over silica gel (monitored by thin layer chromatography) and eluted with 19:1 (v/v) methylene chloride:methanol. Evaporation of the collected fractions yielded a yellow solid that was further purified via recrystallization in EtOAc to yield 13.23 g (75% yield) of tert-butyl 2-(8-oxo-7,8-dihydropyrazino[2,3-d]pyridazin-5-yl)acetate (Compound 2): $^1$H NMR (CDCl$_3$, 300 MHz): $\delta_{ppm}$ 10.3 (br s, 1H), 9.06 (d, J=2.1 Hz, 1H), 9.04 (d, J=2.1 Hz, 1H), 4.02 (s, 2H), 1.43 (s, 9H).

Preparation of tert-butyl 2-(8-oxo-7-((5-(trifluoromethyl)benzo[d]thiazol-2-yl)methyl)-7,8-dihydropyrazino[2,3-d]pyridazin-5-yl)acetate (Compound 4)

To a vigorously stirred solution of 2.5 g (9.54 mmol) of tert-butyl 2-(8-oxo-7,8-dihydropyrazino[2,3-d]pyridazin-5-yl)acetate (Compound 2) in 67 mL of NMP was added 3.12 g (9.09 mmol) of 2-(iodomethyl)-5-(trifluoromethyl)benzo [d]thiazole (Compound 5) and 1.51 g (10.9 mmol) of $K_2CO_3$. The resulting reaction mixture was covered from light and stirred for 5 hours at ambient temperature. Subsequently, to the reaction mixture was added Et$_2$O and water, the layers separated, and the aqueous layer extracted with Et$_2$O (1×). The combined ethereal layers were then washed sequentially with H$_2$O (1×), 1.0 M KOH (1×), 1.0 M $Na_2S_2O_3$ (1×), 1.0 M HCl (1×) and brine (1×). The organic layer was dried over $Na_2SO_4$, filtered and concentrated in vacuo. The residue was purified via flash column chromatography over silica gel (monitored by thin layer chromatography) and eluted with 49:1 (v/v) methylene chloride: methanol. Evaporation of the collected fractions yielded 4.03 g (93% yield) of tert-butyl 2-(8-oxo-7-((5-(trifluoromethyl)benzo[d]thiazol-2-yl)methyl)-7,8-dihydropyrazino[2, 3-d]pyridazin-5-yl)acetate (Compound 4).

Preparation of 2-(8-oxo-7-((5-(trifluoromethyl) benzo[d]thiazol-2-yl)methyl)-7,8-dihydropyrazino[2, 3-d]pyridazin-5-yl)acetic acid (Compound A)

(The deprotection of Compound 4 occurred in two separate flasks, but before workup and purification took place the two reaction mixtures were combined together).
In one flask, 3.09 g (6.49 mmol) of tert-butyl 2-(8-oxo-7-((5-(trifluoromethyl)benzo[d]thiazol-2-yl)methyl)-7,8-dihydropyrazino[2,3-d]pyridazin-5-yl)acetate (Compound 4) was dissolved in 30 mL of formic acid (88% in water) and 3.0 mL of water. In a separate flask, 4.95 g (10.37 mmol) of Compound 4 was dissolved in 48 mL of formic acid (88% in water) and 5.0 mL of water. The reaction mixtures were stirred separately for 22 hours at ambient temperature. The reaction mixtures were concentrated in vacuo and the residues combined. The combined residues were partitioned between Et$_2$O and saturated aqueous $NaHCO_3$, the layers separated, and the aqueous layer extracted with Et$_2$O (1×). The aqueous layer was acidified to pH 2 by addition of conc. HCl and was extracted with EtOAc (3×). The organic layer from the second extraction was dried over $Na_2SO_4$, filtered and concentrated in vacuo. The residue was purified via flash column chromatography over silica gel (monitored by thin layer chromatography) and eluted with 97:3 (v/v) methylene chloride:methanol containing 1% AcOH. Evaporation of the collected fractions yielded 5.29 g (75% yield) of 2-(8-oxo-7-((5-(trifluoromethyl)benzo[d]thiazol-2-yl)methyl)-7,8-dihydropyrazino[2,3-d]pyridazin-5-yl)acetic acid (Compound A) as a solid. The solid can be further purified via recrystallization from MeOH to yield an off-white solid: m.p.=210-211° C. ¹H NMR (acetone-d₆, 400 MHz): $\delta_{ppm}$ 9.19 (d, J=2.0 Hz, 1H), 9.17 (d, J=2.0 Hz, 1H), 8.30-8.27 (m, 2H), 7.74 (dd, J=8 Hz, 1.2 Hz, 1H), 5.90 (s, 2H), 4.12 (s, 2H); ESI-MS 422 (M+H)⁺; m.p.=210-211° C.

Example 3

Preparation of Compound 8

Compound 8, shown below, was prepared as follows:

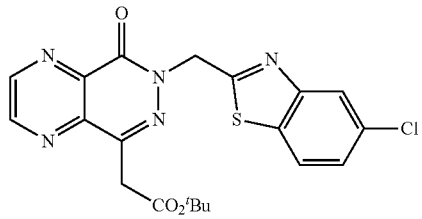

The preparation described for Compound 4 was repeated except that 5-chloro-2-(chloromethyl)-benzo[d]thiazole was the reagent employed in place of 2-(chloromethyl)-5-(trifluoromethyl)benzo[d]thiazole, using the same molar proportions as before. In this case, the final product obtained was tert-butyl 2-(7-((5-chlorobenzo[d]thiazol-2-yl)methyl)-8-oxo-7,8-dihydropyrazino[2,3-d]pyridazin-5-yl)acetate (Compound 8) in 75% yield: ¹H NMR (CDCl₃, 300 MHz): $\delta_{ppm}$ 9.08 (s, 1H), 9.05 (s, 1H), 8.00 (s, 1H), 7.74 (d, J=8.7 Hz, 1H), 7.36 (d, J=8.7 Hz, 1H), 5.87 (s, 2H), 4.04 (s, 2H), 1.41 (s, 9H).

Example 4

Preparation of Compound B

Compound B, shown below, was prepared as follows:

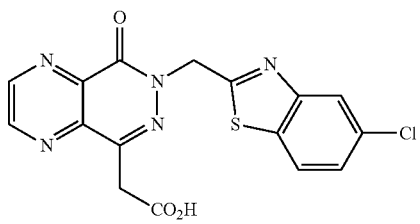

The preparation described for Compound 8 was repeated. The schemes described in Example 1 to obtain Compound A from Compound 4 was carried out, where Compound 4 was replaced with Compound 8. In this case, the final product obtained was 2-(7-((5-chlorobenzo[d]thiazol-2-yl)methyl)-8-oxo-7,8-dihydropyrazino[2,3-d]pyridazin-5-yl)acetic acid (Compound B) in 51% yield: ¹H NMR (DMSO-d₆, 300 MHz): $\delta_{ppm}$ 9.26 (d, J=2.1 Hz, 1H), 9.21 (d, J=2.1 Hz, 1H), 8.13 (d, J=8.7 Hz, 1H), 8.09 (d, J=2.4 Hz, 1H), 7.51 (dd, J=8.7, 2.4 Hz, 1H), 5.83 (s, 2H), 4.02 (s, 2H); m.p.=196-197° C.

Example 5

Preparation of Compound 9

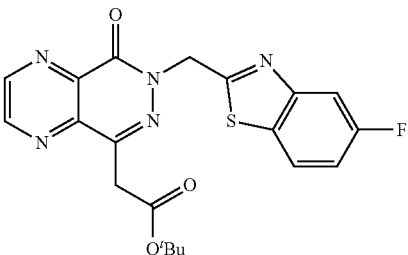

The preparation described for Compound 4 was repeated except that 2-(bromomethyl)-5-fluorobenzo[d]thiazole was the reagent employed in place of 2-(chloromethyl)-5-(trifluoromethyl)benzo[d]thiazole, using the same molar proportions as before. In this case, the final product obtained was tert-butyl 2-(7-((5-fluorobenzo[d]thiazol-2-yl)methyl)-8-oxo-7,8-dihydropyrazino[2,3-d]pyridazin-5-yl)acetate (Compound 9) in 73% yield: ¹H NMR (CDCl₃, 300 MHz): $\delta_{ppm}$ 9.09 (d, J=1.8 Hz, 1H), 9.05 (d, J=1.8 Hz, 1H), 7.77 (dd, J=8.7 Hz, 4.8 Hz, 1H), 7.71 (dd, J=9.3 Hz, 2.7 Hz, 1H), 7.16 (ddd, J=8.7 Hz, 8.7 Hz, 2.7 Hz, 1H), 5.88 (s, 2H), 4.05 (s, 2H), 1.42 (s, 9H).

Example 6

Preparation of Compound 10

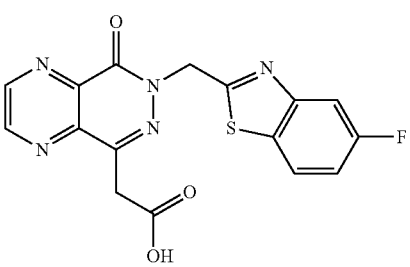

The scheme described in Example 1 to obtain Compound A from Compound 4 was carried out, where Compound 4 was replaced with Compound 9. In this case, the final product obtained was 2-(7-((5-fluorobenzo[d]thiazol-2-yl)methyl)-8-oxo-7,8-dihydropyrazino[2,3-d]pyridazin-5-yl)acetic acid (Compound 10) in 63% yield: ¹H NMR (DMSO-d₆, 300 MHz): $\delta_{ppm}$ 9.25 (d, J=2.1 Hz, 1H), 9.21 (d, J=2.1 Hz, 1H), 8.12 (dd, J=9.0 Hz, 5.7 Hz, 1H), 7.85 (dd, J=9.9 Hz, 2.4 Hz, 1H), 7.36 (ddd, J=9.0 Hz, 9.0 Hz, 2.4 Hz, 1H), 5.82 (s, 2H), 4.02 (s, 2H).

Example 7

Preparation of Compound 11

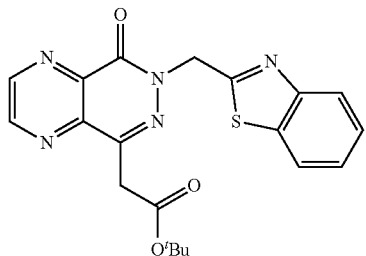

The preparation described for Compound 4 was repeated except that 2-(bromomethyl)benzo[d]thiazole was the reagent employed in place of 2-(chloromethyl)-5-(trifluoromethyl)benzo[d]thiazole, using the same molar proportions as before. In this case, the final product obtained was tert-butyl 2-(7-(benzo[d]thiazol-2-ylmethyl)-8-oxo-7,8-dihydropyrazino[2,3-d]pyridazin-5-yl)acetate (Compound 11) in 63% yield: $^1$H NMR (CDCl$_3$, 300 MHz): $\delta_{ppm}$ 9.07 (d, J=1.8 Hz, 1H), 9.03 (d, J=1.8 Hz, 1H), 8.02 (d, J=7.5 Hz, 1H), 7.83 (d, J=7.5 Hz, 1H), 7.46 (ddd, J=7.5 Hz, 7.5 Hz, 1.2 Hz, 1H), 7.37 (ddd, J=7.5 Hz, 7.5 Hz, 1.2 Hz, 1H), 5.89 (s, 2H), 4.04 (s, 2H), 1.41 (s, 9H).

Example 8

Preparation of Compound 12

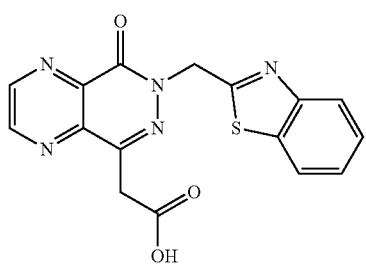

The scheme described in Example 1 to obtain Compound A from Compound 4 was carried out, where Compound 4 was replaced with Compound 11. In this case, the final product obtained was 2-(7-(benzo[d]thiazol-2-ylmethyl)-8-oxo-7,8-dihydropyrazino[2,3-d]pyridazin-5-yl)acetic acid (Compound 12) in 67% yield: $^1$H NMR (DMSO-d$_6$, 300 MHz): $\delta_{ppm}$ 9.26 (d, J=2.1 Hz, 1H), 9.22 (d, J=2.1 Hz, 1H), 8.08 (dd, J=7.5 Hz, 1.2 Hz, 1H), 7.99 (dd, J=8.1 Hz, 1.2 Hz, 1H), 7.52 (ddd, J=8.1 Hz, 8.1 Hz, 1.2 Hz, 1H), 7.45 (ddd, J=7.5 Hz, 7.5 Hz, 1.2 Hz, 1H), 5.83 (s, 2H), 4.03 (s, 2H).

Example 9

Preparation of Compound 13

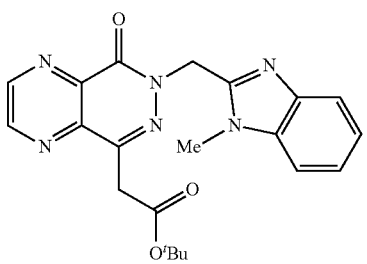

The preparation described for Compound 4 was repeated except that 2-(chloromethyl)-1-methyl-1H-benzo[d]imidazole was the reagent employed in place of 2-(chloromethyl)-5-(trifluoromethyl)benzo[d]thiazole, using the same molar proportions as before. In this case, the final product obtained was tert-butyl 2-(7-((1-methyl-1H-benzo[d]imidazol-2-yl)methyl)-8-oxo-7,8-dihydropyrazino[2,3-d]pyridazin-5-yl)acetate (Compound 13) in 50% yield: $^1$H NMR (CDCl$_3$, 300 MHz): $\delta_{ppm}$ 9.04 (d, J=2.1 Hz, 1H), 9.02 (d, J=2.1 Hz, 1H), 7.74 (dd, J=7.2 Hz, 1.2 Hz, 1H), 7.35 (ddd, J=7.2 Hz, 7.2 Hz, 1.2 Hz, 1H), 7.29-7.22 (m, 2H), 5.77 (s, 2H), 4.05 (s, 2H), 3.97 (s, 3H), 1.40 (s, 9H).

Example 10

Preparation of Compound 14

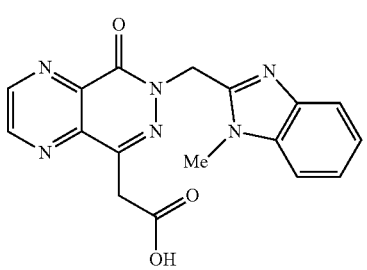

The scheme described in Example 1 to obtain Compound A from Compound 4 was carried out, where Compound 4 was replaced with Compound 13. In this case, the final product obtained was 2-(7-((1-methyl-1H-benzo[d]imidazol-2-yl)methyl)-8-oxo-7,8-dihydropyrazino[2,3-d]pyridazin-5-yl)acetic acid (Compound 14) in 88% yield: $^1$H NMR (DMSO-d$_6$, 300 MHz): $\delta_{ppm}$ 9.26 (d, J=2.1 Hz, 1H), 9.21 (d, J=2.1 Hz, 1H), 7.70 (d, J=8.4 Hz, 1H), 7.61 (d, J=8.1 Hz, 1H), 7.37 (dd, J=7.8 Hz, 7.8 Hz, 1H), 7.29 (dd, J=7.8 Hz, 7.8 Hz, 1H), 5.81 (s, 2H), 4.00 (s, 2H), 3.97 (s, 3H).

Example 11

Preparation of Compound 15

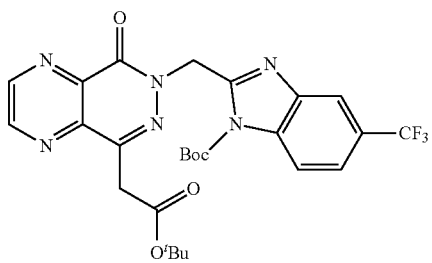

15

To a solution of 0.100 g (0.427 mmol) of 2-(chloromethyl)-5-(trifluoromethyl)-1H-benzo[d]imidazole in 4.0 mL of $CH_2Cl_2$ was added sequentially 0.103 g (0.470 mmol) of $(Boc)_2O$, 0.010 g (0.854 µmol) of DMAP, and 71 µL (0.512 mmol) of TEA. The reaction mixture was stirred at ambient temperature overnight. The reaction mixture was concentrated in vacuo and the residue partitioned between $CH_2Cl_2$ and saturated aqueous $NaHCO_3$. The layers were separated and the organics dried over $Na_2SO_4$, filtered and concentration in vacuo. The crude residue was used without further purification.

The preparation described for Compound 4 was repeated except that the crude residue from above was the reagent employed in place of 2-(chloromethyl)-5-(trifluoromethyl)benzo[d]thiazole, using the same molar proportions as before. In this case, the final product obtained was a mixture of isomers of tert-butyl 2-((8-(2-(tert-butoxy)-2-oxoethyl)-5-oxopyrazino[2,3-d]pyridazin-6(5H)-yl)methyl)-5-(trifluoromethyl)-1H-benzo[d]imidazole-1-carboxylate (Compound 15) in 44% yield: $^1$H NMR (CDCl$_3$, 300 MHz): $\delta_{ppm}$ 9.09-9.06 (m, 4H), 8.26 (s, 1H), 8.03 (m, 1H), 7.83 (s, 1H), 7.64-7.50 (m, 3H), 5.96 (s, 4H), 4.04 (s, 4H), 1.76 (s, 18H), 1.42 (s, 18H).

Example 12

Preparation of Compound 16

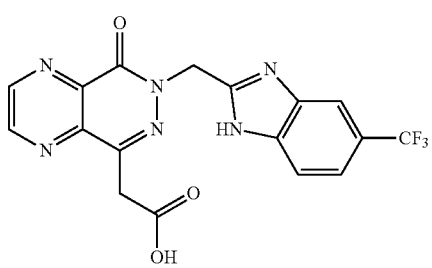

16

The scheme described in Example 1 to obtain Compound A from Compound 4 was carried out, where Compound 4 was replaced with Compound 15. In this case, the final product obtained was 2-(8-oxo-7-((5-(trifluoromethyl)-1H-benzo[d]imidazol-2-yl)methyl)-7,8-dihydropyrazino[2,3-d]pyridazin-5-yl)acetic acid (Compound 16) in 68% yield: $^1$H NMR (DMSO-d$_6$, 300 MHz): $\delta_{ppm}$ 9.26 (d, J=2.1 Hz, 1H), 9.21 (d, J=2.1 Hz, 1H), 7.88 (s, 1H), 7.69 (d, J=8.4 Hz, 1H), 7.49 (d, J=8.4 Hz, 1H), 5.67 (s, 2H), 4.00 (s, 2H).

Example 13

Preparation of Compound 17

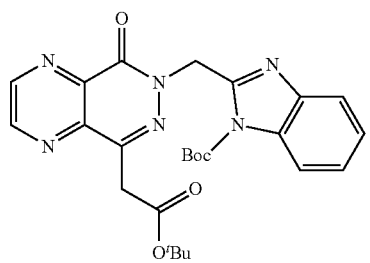

17

The preparation described for Compound 4 was repeated except that tert-butyl 2-(chloromethyl)-1H-benzo[d]imidazole-1-carboxylate was the reagent employed in place of 2-(chloromethyl)-5-(trifluoromethyl)benzo[d]thiazole, using the same molar proportions as before. In this case, the final product obtained was tert-butyl 2-((8-(2-(tert-butoxy)-2-oxoethyl)-5-oxopyrazino[2,3-d]pyridazin-6(5H)-yl)methyl)-1H-benzo[d]imidazole-1-carboxylate (Compound 17) in 81% yield: $^1$H NMR (CDCl$_3$, 300 MHz): $\delta_{ppm}$ 9.08 (d, J=2.1 Hz, 1H), 9.04 (d, J=2.1 Hz, 1H), 7.92 (d, J=8.7 Hz, 1H), 7.54 (d, J=7.5 Hz, 1H), 7.33-7.22 (m, 2H), 5.95 (s, 2H), 4.04 (s, 2H), 1.74 (s, 9H), 1.41 (s, 9H).

Example 14

Preparation of Compound 18

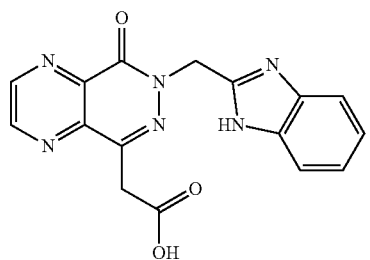

18

The scheme described in Example 1 to obtain Compound A from Compound 4 was carried out, where Compound 4 was replaced with Compound 17. In this case, the final product obtained was 2-(7-((1H-benzo[d]imidazol-2-yl)methyl)-8-oxo-7,8-dihydropyrazino[2,3-d]pyridazin-5-yl)acetic acid (Compound 18) in 69% yield: $^1$H NMR (DMSO-d$_6$, 300 MHz): $\delta_{ppm}$ 9.26 (d, J=2.1 Hz, 1H), 9.21 (d, J=2.1 Hz, 1H), 7.56-7.53 (m, 2H), 7.24-7.20 (m, 2H), 5.66 (s, 2H), 4.00 (s, 2H).

Example 15

Preparation of Compound 19

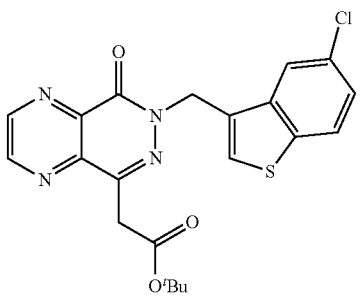

The preparation described for Compound 4 was repeated except that 3-(bromomethyl)-5-chlorobenzo[b]thiophene was the reagent employed in place of 2-(chloromethyl)-5-(trifluoromethyl)benzo[d]thiazole, using the same molar proportions as before. In this case, the final product obtained was tert-butyl 2-(7-((5-chlorobenzo[b]thiophen-3-yl)methyl)-8-oxo-7,8-dihydropyrazino[2,3-d]pyridazin-5-yl)acetate (Compound 19) in 69% yield: $^1$H NMR (CDCl$_3$, 300 MHz): $\delta_{ppm}$ 9.02 (s, 1H), 8.98 (s, 1H), 8.19 (d, J=1.8 Hz, 1H), 7.73-7.70 (m, 2H), 7.30-7.27 (m, 1H), 5.63 (s, 2H), 4.02 (s, 2H), 1.40 (s, 9H).

Example 16

Preparation of Compound 20

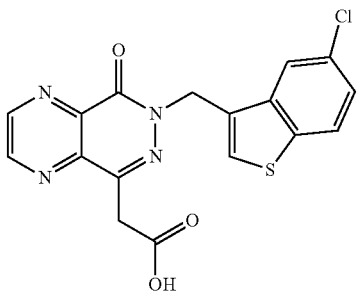

The scheme described in Example 1 to obtain Compound A from Compound 4 was carried out, where Compound 4 was replaced with Compound 19. In this case, the final product obtained was 2-(7-((5-chlorobenzo[b]thiophen-3-yl)methyl)-8-oxo-7,8-dihydropyrazino[2,3-d]pyridazin-5-yl)acetic acid (Compound 20) in 80% yield: $^1$H NMR (DMSO-d$_6$, 300 MHz): $\delta_{ppm}$ 9.19 (d, J=1.8 Hz, 1H), 9.16 (d, J=1.8 Hz, 1H), 8.18 (d, J=1.8 Hz, 1H), 8.03 (d, J=8.4 Hz, 1H), 7.79 (s, 1H), 7.41 (dd, J=8.4 Hz, 1.8 Hz, 1H), 5.59 (s, 2H), 3.97 (s, 2H).

Example 17

Preparation of Compound 21

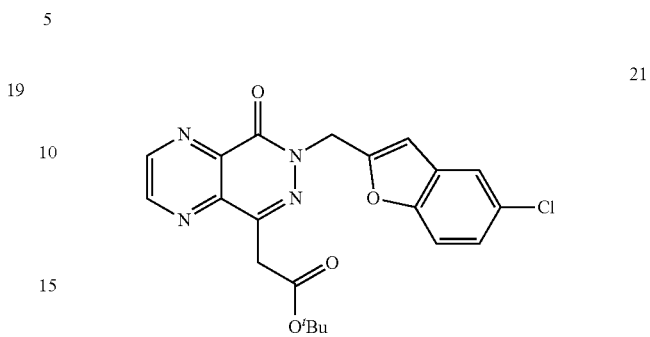

The preparation described for Compound 4 was repeated except that 5-chloro-2-(chloromethyl)benzofuran was the reagent employed in place of 2-(chloromethyl)-5-(trifluoromethyl)benzo[d]thiazole, using the same molar proportions as before. In this case, the final product obtained was tert-butyl 2-(7-((5-chlorobenzofuran-2-yl)methyl)-8-oxo-7,8-dihydropyrazino[2,3-d]pyridazin-5-yl)acetate (Compound 21) in 60% yield: $^1$H NMR (CDCl$_3$, 300 MHz): $\delta_{ppm}$ 9.06 (s, 1H), 9.02 (s, 1H), 7.48 (d, J=2.1 Hz, 1H), 7.33 (d, J=8.7 Hz, 1H), 7.19 (dd, J=8.7 Hz, 2.1 Hz, 1H), 6.76 (s, 1H), 5.59 (s, 2H), 4.03 (s, 2H), 1.41 (s, 9H).

Example 18

Preparation of Compound 22

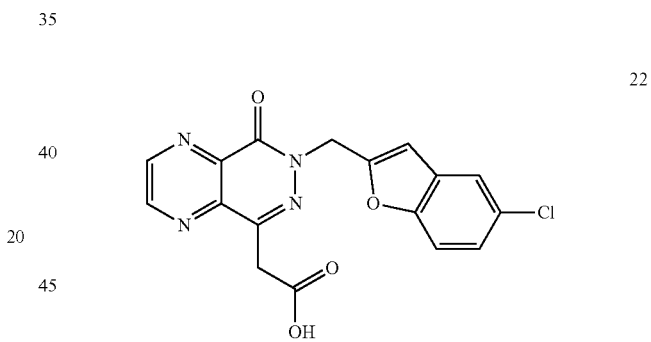

The scheme described in Example 1 to obtain Compound A from Compound 4 was carried out, where Compound 4 was replaced with Compound 21. In this case, the final product obtained was 2-(7-((5-chlorobenzofuran-2-yl)methyl)-8-oxo-7,8-dihydropyrazino[2,3-d]pyridazin-5-yl)acetic acid (Compound 22) in 74% yield: $^1$H NMR (DMSO-d$_6$, 300 MHz): $\delta_{ppm}$ 9.22 (d, J=2.1 Hz, 1H), 9.19 (d, J=2.1 Hz, 1H), 7.68 (d, J=2.1 Hz, 1H), 7.58 (d, J=8.7 Hz, 1H), 7.30 (dd, J=8.7 Hz, 2.1 Hz, 1H), 6.91 (s, 1H), 5.56 (s, 2H), 3.98 (s, 2H).

Example 19

Solubility Study of Compound A Versus Zopolrestat in Buffer

Compound A exhibited superior solubility properties over that of zopolrestat (shown below) when dissolved in Krebs-Henseleit buffer containing (in mM) NaCl 118, KCl 4.7, CaCl$_2$ 2.5, MgCl$_2$ 1.2, NaHCO$_3$ 25, glucose 5, palmitate 0.4, bovine serum albumin 0.4, and 70 mU/L insulin.

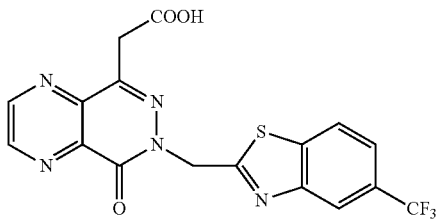

Compound A

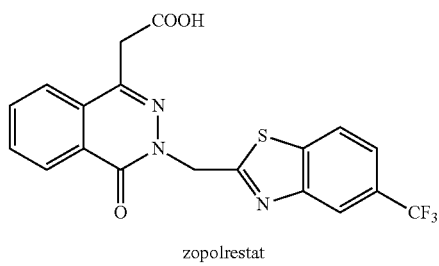

zopolrestat

Compound A, when added to the Krebs-Henseleit buffer, was soluble without any precipitation or turbidity. In the case of zopolrestat, heat was applied to render zopolrestat soluble in the Krebs-Henseleit buffer. These results show improved solubility of Compound A over that of zopolrestat.

Example 20

Solubility Study of Compound A Versus Zopolrestat in Water

Each sample of Compound A & zopolrestat were placed, separately, in water (MQW ultra nanopure) at ambient temperature and vortexed for 3 minutes. The aliquots were then filtered through a tightly-packed cotton plug (placed in a pipette) to remove any residual solids. The attempted concentrations of the respective solutions of Compound A and zopolrestat made were 0.05 mg/mL, 0.1 mg/mL, 0.5 mg/mL, 1.0 mg/mL, 5.0 mg/mL, and 10.0 mg/mL. The pH of the water used was 7.1 (measured electronically by an Orion perpHect LogR Meter Model #370).

The filtered samples were run through a binary gradient (program: 5%-100% MeCN over 30 mins) on a LC-MS (Shimadzu LCMS-2010A Liquid Chromatography Mass Spectrometer, reverse-phase column) A 5 μL volume of each sample solution was injected for each run. Each trace contained a peak (for Compound A, T$_R$ approx. 14.070 mins; for zopolrestat, T$_R$ approx. 16.666 mins) measured at a wavelength of 254 nm for which the respective parent ion masses were observed.

By comparing the absorbance areas under the peaks corresponding to Compound A & zopolrestat in each water solution made (Table 1), a solubility curve for each compound was generated (FIG. 1). The measured data, and generated solubility curves, show that Compound A possesses a significantly greater solubility in pH 7.1 water than Zopolrestat at ambient temperature at all concentration.

TABLE 1

Integration of Absorbance Peaks for Various Concentrations of Compounds.

| Compound A (mg/mL) | Area | Zopolrestat (mg/mL) | Area |
|---|---|---|---|
| 0.05 | 1811131 | 0.05 | 1039247 |
| 0.1 | 3221003 | 0.1 | 1899466 |
| 0.5 | 5814304 | 0.5 | 4304556 |
| 1 | 10515430 | 1 | 6129559 |
| 5 | 17216187 | 5 | 13314544 |
| 10 | 20397336 | 10 | 13362465 |

Example 21

In Vitro Studies of Compound A Versus Zopolrestat

The reductase activity of Compound A and zopolrestat were spectrophotometrically assayed by following the decrease of NADPH at 25° C. for 4 min as described in Sato, S. (1992), "Rat kidney aldose reductase and aldehyde reductase and polyolproduction in rat kidney" *Am. J. Physiol.* 263, F799.F805, incorporated by reference herein in its entirety.

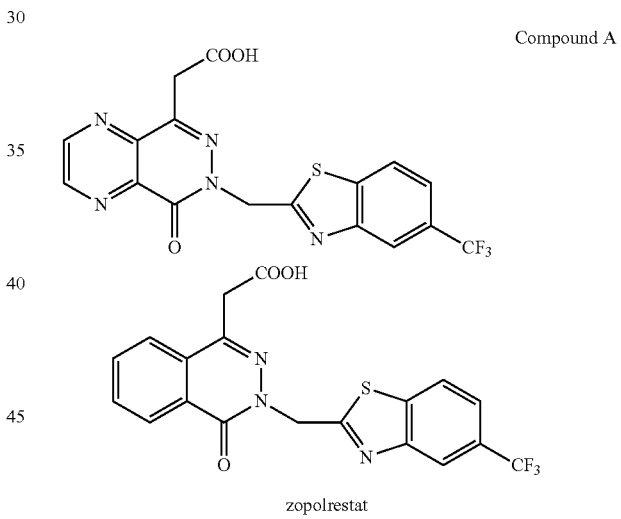

Figure 2:
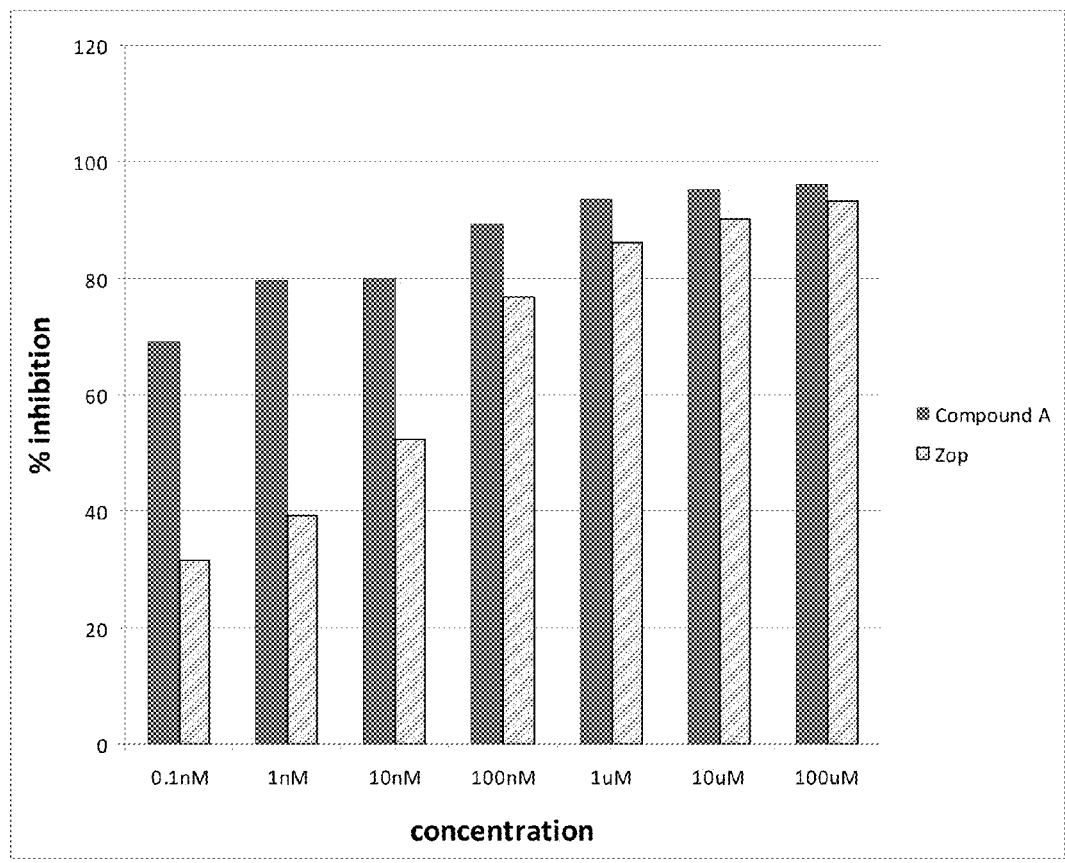
FIG. 2 shows aldose reductase inhibitory activity for Compound A and zopolrestat.

Briefly, the reaction mixture (total volume 1 ml) contained 0.1 mM NADPH, 100 mM substrate (DL-glyceraldehyde or L-xylose) and human recombinant aldose reductase (100 mU) in 0.1 M phosphate buffer, pH 6.2. The head to head experiment was carried out in a microplate assay for AR inhibition using D-Glyceraldehyde and NADPH and the absorbance changes were monitored at 340 nm and % inhibition was calculated for ARIs at concentrations ranging from 0.1 nM to 100 μM (Table 2 and FIG. 2). Data is presented as mean±standard deviation and is an average of 5 separate runs. The reaction was started by adding the substrate (glyceraldehyde or xylose) as well as the same reaction mixture in which the substrate replaced by deionized water was used as a control. One enzyme unit (U) was defined as the activity consuming 1 μmole of NADPH per min at 25° C.

TABLE 2

Aldose Reductase Activity for Zopolrestat and Compound A.

| Concentration | % Inhibition (zopolrestat) | % Inhibition (Compound A) |
| --- | --- | --- |
| 1 pM | 11.0 | |
| 10 pM | 29.0 | |
| 0.1 nM | 31.7 ± 5.1 | 69.0 ± 1.3 |
| 1 nM | 39.3 ± 4.3 | 79.6 ± 2.4 |
| 10 nM | 52.2 ± 1.9 | 80.0 ± 1.8 |
| 100 nM | 76.7 ± 2.7 | 89.2 ± 0.7 |
| 1 μM | 86.3 ± 3.6 | 93.6 ± 2.8 |
| 10 μM | 90.1 ± 3.4 | 95.3 ± 1.1 |
| 100 μM | 93.2 ± 3.8 | 96.2 ± 3.3 |

Figure 3:
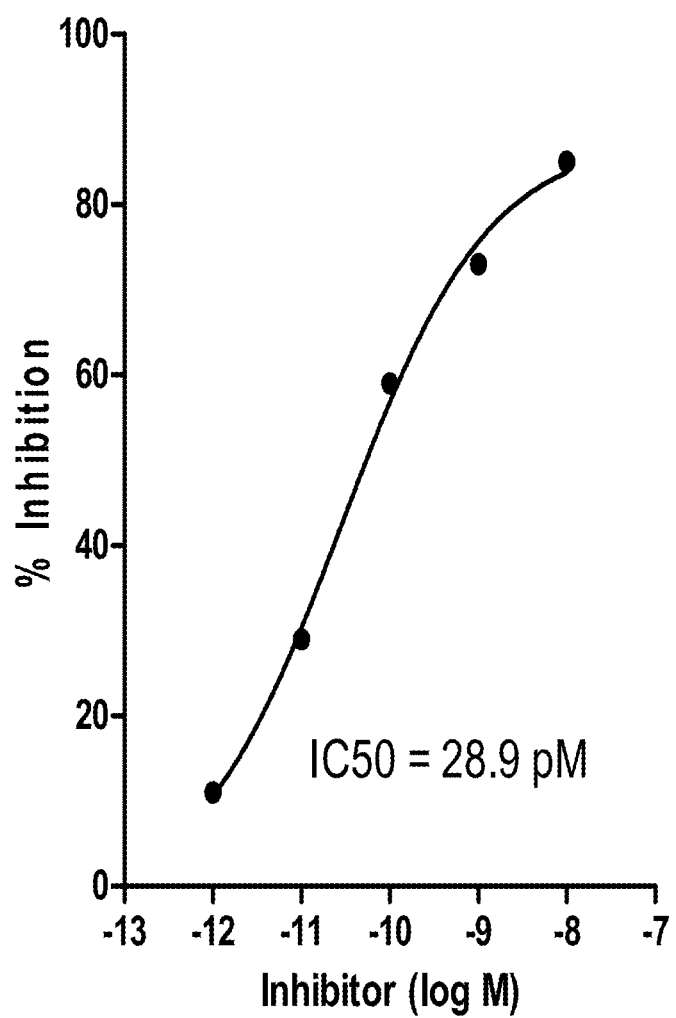
FIG. 3 shows the concentration versus inhibition of aldose reductase curve for Compound A.

Results show a significant increase in inhibition potency of Compound A over that of zopolrestat. The concentration versus inhibition curve for Compound A is shown in FIG. 3, and Compound A shows an $IC_{50}$ of 28.9 picomolar for aldose reductase. Compound A is approximately 100× more active than zopolrestat in vitro against aldose reductase.

Example 22

Ex Vivo Studies of Compound A

All rat studies were performed with the approval of the Institutional Animal Care and Use Committee at Columbia University, New York. This investigation conforms to the *Guide for the Care and Use of Laboratory Animals* published by the US National Institutes of Health (NIH publication No. 85-23, 1996; hereby incorporated by reference in its entirety).

Experiments were performed using an isovolumic isolated rat heart preparation as as described by Hwang Y C, Sato S, Tsai J Y, Yan S, Bakr S, Zhang H, Oates P J, Ramasamy R (2002), "Aldose reductase activation is a key component of myocardial response to ischemia,"*Faseb J.* 16, 243-245 and Ramasamy R, Hwang Y C, Whang J, Bergmann S R (2001), "Protection of ischemic hearts by high glucose is mediated, in part, by GLUT-4," *American Journal of Physiology.* 281, H290-297; each of which hereby incorporated by reference in its entirety.

Male Wistar rats (300.350 g, 3 to 4 months old) were anesthetized with a mixture of ketamine (80 mg/kg) and xylazine (10 mg/kg). After deep anesthesia was achieved, hearts were rapidly excised, placed into iced saline, and retrogradely perfused at 37° C. in a non-recirculating mode through the aorta at a rate of 12.5 ml/min. Hearts were perfused with modified Krebs-Henseleit buffer containing (in mM) NaCl 118, KCl 4.7, $CaCl_2$ 2.5, $MgCl_2$ 1.2, $NaHCO_3$ 25, glucose 5, palmitate 0.4, bovine serum albumin 0.4, and 70 mU/L insulin. The perfusate was equilibrated with a mixture of 95% $O_2$-5% $CO_2$, which maintained perfusate $Po_2$>600 mmHg Left ventricular developed pressure (LVDP) and left ventricular end diastolic pressure (LVEDP) were measured using a latex balloon in the left ventricle. LVDP, heart rate, and coronary perfusion pressure were monitored continuously on a ADI recorder. All rat hearts subjected to 20 min of zero-flow ischemia and 60 min of reperfusion (I/R).

In studies involving the use of aldose reductase inhibitor, hearts were perfused with modified Krebs-Henseleit buffer containing Compound A (shown below), at a final concentration of 100 nM, 10 min prior to ischemia and was continued throughout the perfusion protocol. Creatine kinase (CK) release, a marker of myocardial I/R injury, was measured as described by Hwang Y C, Sato S, Tsai J Y, Yan S, Bakr S, Zhang H, Oates P J, Ramasamy R (2002), "Aldose reductase activation is a key component of myocardial response to ischemia,"*Faseb J.* 16, 243-245 and Ramasamy R, Hwang Y C, Whang J, Bergmann S R (2001), "Protection of ischemic hearts by high glucose is mediated, in part, by GLUT-4," *American journal of physiology.* 281, H290-297; each of which hereby incorporated by reference in its entirety.

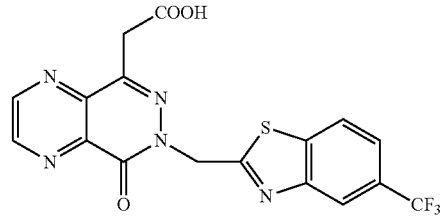

Compound A

Briefly, isolated perfused hearts were subjected to ischemia reperfusion (I/R) injury and the measures of cardiac injury and cardiac function monitored. Creatine kinase (CK) release during reperfusion, a marker of cardiac ischemic injury, was reduced in rat hearts treated with Compound A than in untreated hearts (Table 3A). Left ventricular developed pressure (LVDP) recovery was greater in rat hearts treated with Compound A compared to the untreated hearts after I/R (Table 3B), indicating improved functional recovery in Compound A treated hearts.

TABLE 3

A) CK Release (expressed as IU/g wet weight)
Untreated Rat hearts = 939 ± 146
Compound A treated Rat hearts = 425 ± 63
B) LVDP Recovery (expressed as % of pre-ischemic values)
Untreated Rat hearts = 48 ± 7
Compound A Treated Rat Hearts = 76 ± 5

Although the invention has been described and illustrated in the foregoing illustrative embodiments, it is understood that the present disclosure has been made only by way of example, and that numerous changes in the details of implementation of the invention can be made without departing from the spirit and scope of the invention, which is limited only by the claims that follow. Features of the disclosed embodiments can be combined and rearranged in various ways within the scope and spirit of the invention.

What is claimed is:

1. A method of treating a subject with evolving myocardial infarction comprising: administering a therapeutically effective amount of a compound of formula (I)

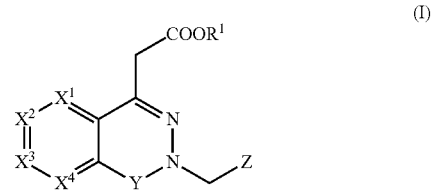

wherein,
R¹ is H;
X¹ is N;
X² is CH;
X³ is CH;
X⁴ is N ;
Y is a C=O, C=S, C=NH, or C=N(C₁C₄)-alkyl;
Z is

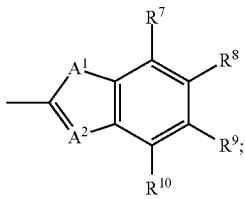

A¹ is S;
A² is N; and
R⁷ through R¹⁰ are independently hydrogen, halogen, cyano, acyl, haloalkyl, haloalkoxy, haloalkylthio, trifluoroacetyl, (C₁-C₄)-alkyl, (C₁-C₄)-alkoxy, (C₁-C₄)-alkylthio, (C₁-C₄)-alkylsulfinyl, or (C₁-C₄)-alkylsulfonyl; or two of R⁷ through R¹⁰ taken together are (C₁-C₄)-alkylenedioxy;
or a pharmaceutically acceptable salt or solvate thereof;
to a subject in need thereof.

2. The method of claim 1, wherein
Y is C=O; and
R⁷ through R¹⁰ are independently hydrogen, halogen, cyano, acyl, haloalkyl, haloalkoxy, haloalkylthio, (C₁-C₄)-alkyl, (C₁-C₄)-alkoxy, (C₁-C₄)-alkylthio, (C₁-C₄)-alkylsulfinyl, or (C₁-C₄)-alkylsulfonyl.

3. The method of claim 2, wherein
R⁷ through R¹⁰ are independently hydrogen, halogen, or haloalkyl.

4. The method of claim 1, wherein the compound of formula (I) is

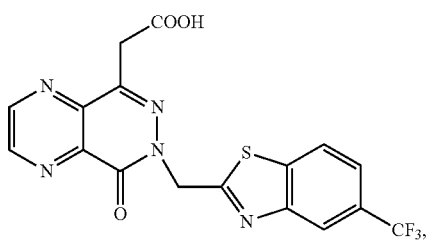

or a pharmaceutically acceptable salt thereof.

5. The method of claim 1, wherein the compound of formula (I) is

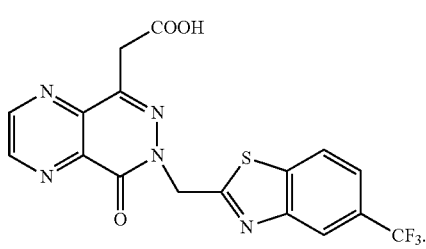 [SMILES: O=C(O)Cc1nn(Cc2nc3cc(C(F)(F)F)ccc3s2)c(=O)c2nccnc12]

6. The method of claim 1, wherein the compound of formula (I) is

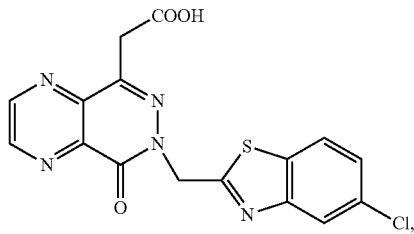

or a pharmaceutically acceptable salt or solvate thereof.

7. The method of claim 1, wherein the compound of formula (I) is

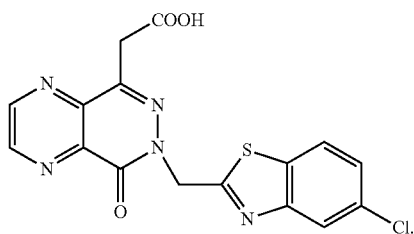 [SMILES: O=C(O)Cc1nn(Cc2nc3cc(Cl)ccc3s2)c(=O)c2nccnc12]

8. The method of claim 1, wherein the subject is a human.
9. The method of claim 4, wherein the subject is a human.
10. The method of claim 5, wherein the subject is a human.
11. A method of treating a subject with evolving myocardial infarction comprising: administering a therapeutically effective amount of a pharmaceutical composition comprising a compound of formula (I)

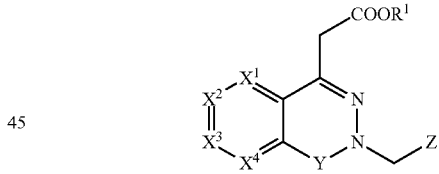

wherein,
R¹ is H;
X¹ is N;
X² is CH;
X³ is CH;
X⁴ is N;
Y is a C=O, C=S, C=NH, or C=N(C₁-C₄)-alkyl;
Z is

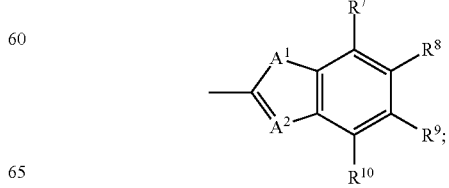

A¹ is S;
A² is N; and
R⁷ through R¹⁰ are independently hydrogen, halogen, cyano, acyl, haloalkyl, haloalkoxy, haloalkylthio, trifluoroacetyl, $(C_1-C_4)$-alkyl, $(C_1-C_4)$-alkoxy, $(C_1-C_4)$-alkylthio, $(C_1-C_4)$-alkylsulfinyl, or $(C_1-C_4)$-alkylsulfonyl; or two of R⁷ through R¹⁰ taken together are $(C_1-C_4)$-alkylenedioxy;
or a pharmaceutically acceptable salt or solvate thereof; and
a pharmaceutically acceptable carrier, to a subject in need thereof.

12. The method of claim 11, wherein
Y is C=O; and
R⁷ through R¹⁰ are independently hydrogen, halogen, cyano, acyl, haloalkyl, haloalkoxy, haloalkylthio, $(C_1-C_4)$-alkyl, $(C_1-C_4)$-alkoxy, $(C_1-C_4)$-alkylthio, $(C_1-C_4)$-alkylsulfinyl, or $(C_1-C_4)$-alkylsulfonyl.

13. The method of claim 12, wherein
R⁷ through R¹⁰ are independently hydrogen, halogen, or haloalkyl.

14. The method of claim 11, wherein the compound of formula (I) is

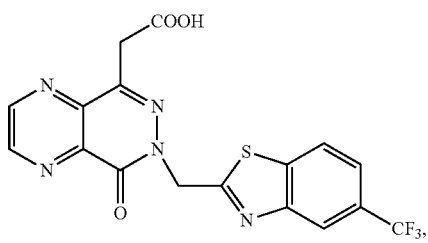 [SMILES: O=C(O)Cc1nn(Cc2nc3cc(C(F)(F)F)ccc3s2)c(=O)c2nccnc12]

or a pharmaceutically acceptable salt thereof.

15. The method of claim 11, wherein the compound of formula (I) is

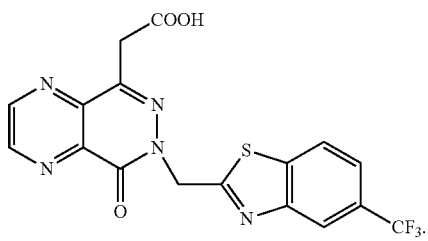 [SMILES: O=C(O)Cc1nn(Cc2nc3cc(C(F)(F)F)ccc3s2)c(=O)c2nccnc12]

16. The method of claim 11, wherein the compound of formula (I) is

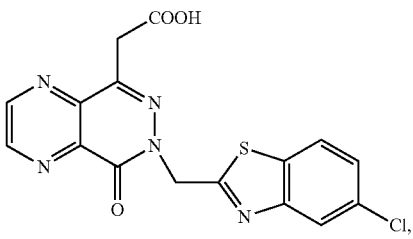

or a pharmaceutically acceptable salt or solvate thereof.

17. The method of claim 11, wherein the compound of formula (I) is

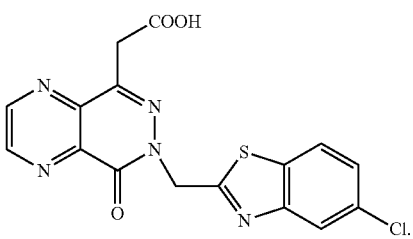 [SMILES: O=C(O)Cc1nn(Cc2nc3cc(Cl)ccc3s2)c(=O)c2nccnc12]

18. The method of claim 11, wherein the subject is a human.

19. The method of claim 14, wherein the subject is a human.

20. The method of claim 15, wherein the subject is a human.

21. The method of claim 6, wherein the subject is a human.

22. The method of claim 7, wherein the subject is a human.

23. The method of claim 16, wherein the subject is a human.

24. The method of claim 17, wherein the subject is a human.

* * * * *

UNITED STATES PATENT AND TRADEMARK OFFICE
CERTIFICATE OF CORRECTION

PATENT NO. : 9,650,383 B2
APPLICATION NO. : 14/541365
DATED : May 16, 2017
INVENTOR(S) : Andrew Wasmuth et al.

It is certified that error appears in the above-identified patent and that said Letters Patent is hereby corrected as shown below:

In the Specification

Column 1, Line 24, the following paragraph should be added:
GOVERNMENT SUPPORT
This invention was made with government support under grant RR024156 awarded by the NIH. The government has certain rights in the invention.

Signed and Sealed this
Twenty-first Day of August, 2018

Andrei Iancu
*Director of the United States Patent and Trademark Office*